United States Patent
Wallace et al.

(10) Patent No.: US 11,725,238 B2
(45) Date of Patent: Aug. 15, 2023

(54) MEASUREMENT OF ANALYTES WITH MEMBRANE CHANNEL MOLECULES, AND BILAYER ARRAYS

(71) Applicant: OXFORD UNIVERSITY INNOVATION LIMITED, Oxford (GB)

(72) Inventors: Mark Wallace, Oxfordshire (GB); Hagan Bayley, Oxfordshire (GB); Shuo Huang, Oxford (GB); Oliver Kieran Castell, Cardiff (GB); Mercedes Romero-Ruiz, Oxfordshire (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 422 days.

(21) Appl. No.: 16/933,184

(22) Filed: Jul. 20, 2020

(65) Prior Publication Data

US 2021/0095338 A1     Apr. 1, 2021

Related U.S. Application Data

(63) Continuation of application No. 15/326,109, filed as application No. PCT/GB2015/051996 on Jul. 9, 2015, now Pat. No. 10,822,655.

(60) Provisional application No. 62/024,315, filed on Jul. 14, 2014.

(51) Int. Cl.
| | |
|---|---|
| *C12Q 1/6874* | (2018.01) |
| *G01N 33/487* | (2006.01) |
| *C12Q 1/6869* | (2018.01) |
| *G01N 21/77* | (2006.01) |

(52) U.S. Cl.
CPC ......... *C12Q 1/6874* (2013.01); *C12Q 1/6869* (2013.01); *G01N 21/77* (2013.01); *G01N 33/48721* (2013.01)

(58) Field of Classification Search
None
See application file for complete search history.

(56) References Cited

PUBLICATIONS

Castell et al., "Quantification of Membrane Protein Inhibition by Optical Ion Flux in a Droplet Interface Bilayer Array," Angew. Chem. Int. Ed. 2012, 51:3134-3138. (Year: 2012).*
Huang et al. "High-throughput optical sensing of nucleic acids in a nanopore array." Nature Nanotechnology 10(11): 986-991 (2015).
Jeon et al. "Hydrogel-encapsulated lipid membranes." Journal of the American Chemical Society 128(1): 42-43 (2006).
Kang et al. "A storable encapsulated bilayer chip containing a single protein nanopore." Journal of the American Chemical Society 129(15): 4701-4705 (2007).
Bayley et al., "Droplet interface bilayers", Mol Biosyst, 4(12):1191-208 (2008).
Branton et al., "The potential and challenges of nanopore sequencing", Nat Biotechnol, 26(10):1146-53 (2008).
Castell et al., "Quantification of Membrane Potein Inhibition by Optical Ion flux in a Droplet Interface Bilayer Array," Angew. Chem. Int. Ed., 51, 3134-3138, (2012).
Cherf et al., "Automated forward and reverse ratcheting of DNA in a nanopore at 5-Å precision precision", Nat Biotechnol, 30(4):344-8 (2012).
Clarke et al., "Continuous base identification for single-molecule nanopore DNA sequencing", Nat Nanotechnol, 4(4):265-70 (2009).
Heron et al., "Simultaneous measurement of ionic current and fluorescence from single protein pores", J Am Chem Soc, 131(5):1652-3 (2009).
Heron et al., "Simultaneous measurement of ionic current and fluorescence from single protein pores", JACS Communications, 131:S1-S8, (2009) Retrieved from the Internet:URL:http://pubs.acs.org/doi/suppl/10.1021/ja808128s/suppl_file/ja808128s_si_001.pdf.
Ide et al., "Simultaneous Optical and Electrical Recording of Single Molecule Bonding to Single Channel Proteins," ChemPhysChem, 11, 3408-3411, (2010).
Leptihn et al., "Constructing droplet interface bilayers from the contact of aqueous droplets in oil", Nat Protoc, 8(6):1048-57 (2013).
Manrao et al., "Reading DNA at single-nucleotide resolution with a mutant MspA nanopore and phi29 DNA polymerase", Nat Biotechnol, 30(4):349-53 (2012).
Mcnally et al., "Optical recognition of converted DNA nucleotides for single-molecule DNA sequencing using nanopore arrays", Nano Lett, 10(6):2237-44 (2010).
Osaki et al., "Multichannel simultaneous measurements of single-molecule translocation in alpha-hemolysin nanopore array", Anal Chem, 81(24):9866-70 (2009).
Stoddart et al., "Single-nucleotide discrimination in immobilized DNA oligonucleotides with a biological nanopore", Proc Natl Acad Sci U S A, 106(19):7702-7 (2009).
Thompson et al., "Rapid assembly of a multimeric membrane protein pore", Biophys J, 101(11):2679-83 (2011).
Venkatesan et al., "Nanopore sensors for nucleic acid analysis", Nat Nanotechnol, 6(10):615-24 (2011).

* cited by examiner

*Primary Examiner* — Kaijiang Zhang
(74) *Attorney, Agent, or Firm* — Nixon Peabody LLP; Mark J. Fitzgerald; Jeanne Jodoin

(57) ABSTRACT

The invention relates to a method for detection of analyte interaction with a channel molecule held in a membrane, comprising the optical detection of a modification in the flux of a signal molecule as it passes through the channel molecule by the action of a membrane potential, wherein the modification in the flux is caused by at least partial blockage of the channel molecule by the analyte. The invention further relates to bilayer arrays, components, methods of manufacture and use.

22 Claims, 30 Drawing Sheets

Figure 1:
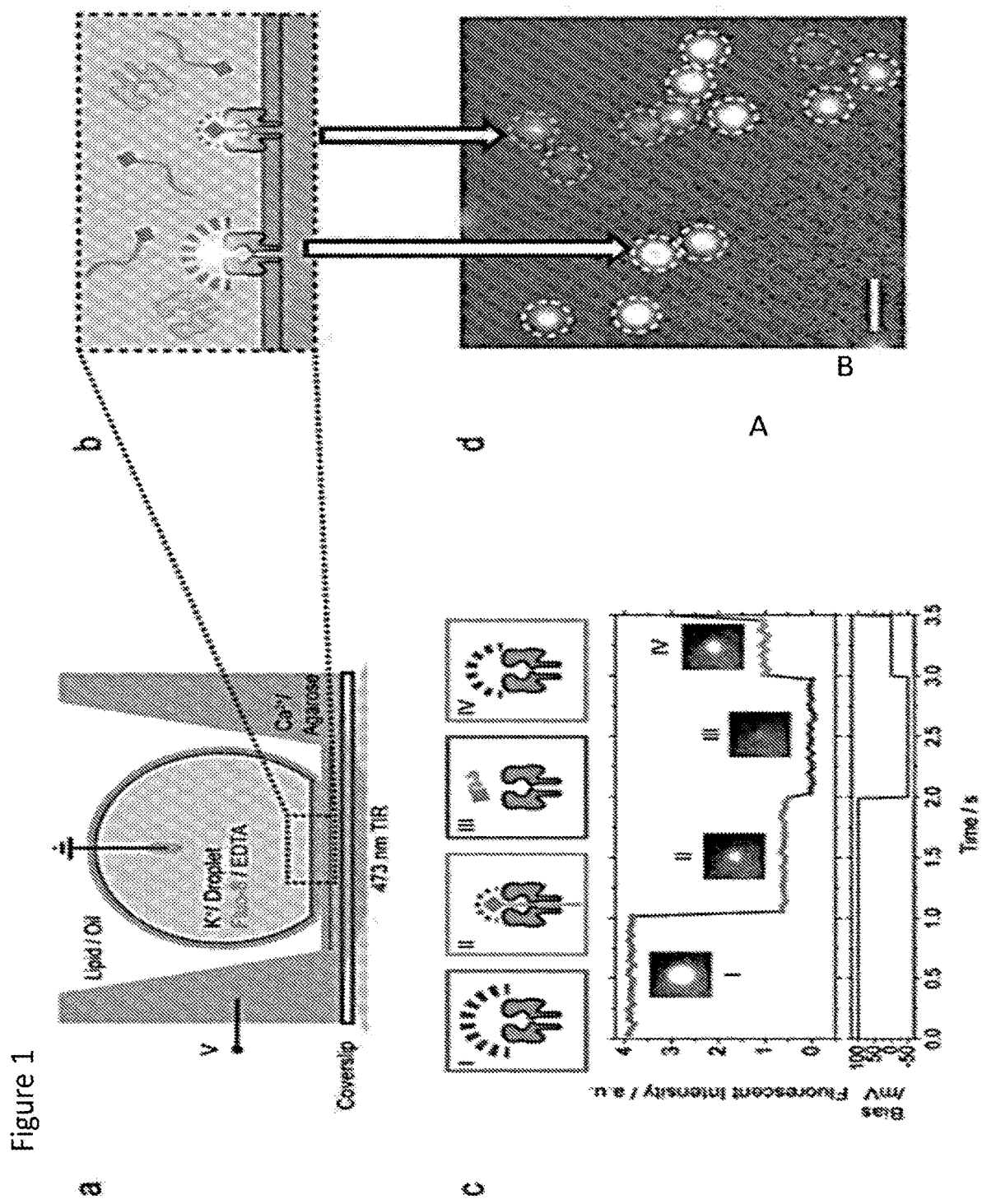
Figure 1:
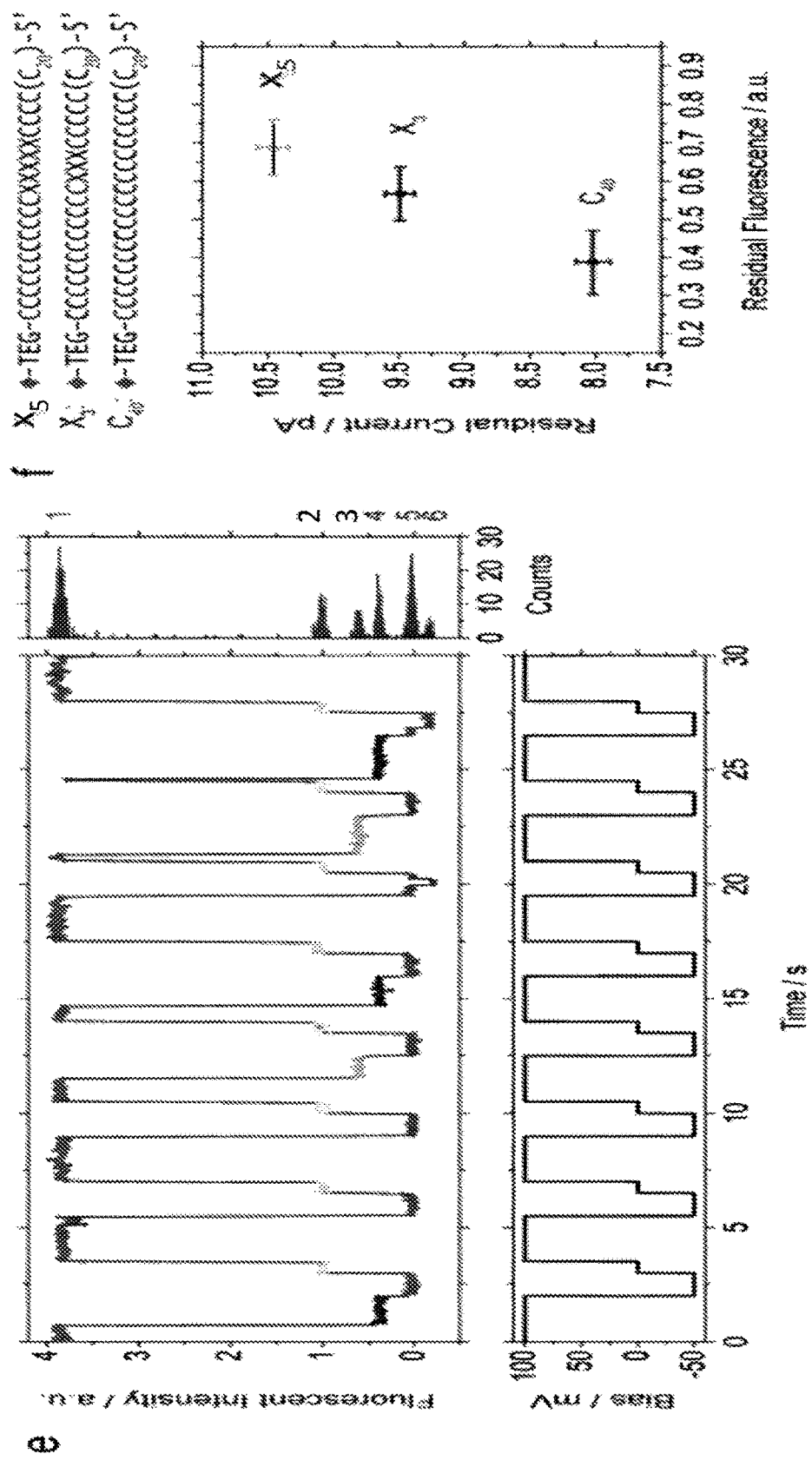

Specification includes a Sequence Listing.

a b

MEASUREMENT OF ANALYTES WITH MEMBRANE CHANNEL MOLECULES, AND BILAYER ARRAYS

CROSS-REFERENCE TO RELATED APPLICATIONS

This application is a continuation under 35 U.S.C. § 120 of co-pending U.S. application Ser. No. 15/326,109 filed Jan. 31, 2017 now U.S. Pat. No. 10,822,655 issued Nov. 3, 2020 which is a 35 U.S.C. § 371 National Phase Entry Application of International Application No. PCT/GB2015/051996 filed Jul. 9, 2015, which designated the U.S., and claims benefit under 35 U.S.C. § 119(e) of U.S. Provisional No. 62/024,315, filed Jul. 14, 2014 the contents of which are incorporated herein by reference in their entireties.

This invention relates to analysis of analytes, such as biological molecules, by channel molecules in a membrane. The invention further relates to a bilayer array, components thereof, and the manufacture and use of a bilayer array.

Acknowledgement of Government Funding

This invention was made with government funds under Grant No. R01 HG003709 awarded by National Institutes of Health. The US Government has rights in the invention.

INCORPORATION BY REFERENCE

The description refers to various publications, the contents of which are incorporated herein by reference.

SEQUENCE LISTING

The instant application contains a Sequence Listing which has been submitted electronically in ASCII format and is hereby incorporated by reference in its entirety. Said ASCII copy, created on Sep. 10, 2020, is named 052342-088740-US_SL.txt and is 3,407 bytes in size.

INTRODUCTION

Transmembrane pores (nanopores) have great potential as direct, electrical biosensors for polymers and a variety of small molecules. In particular, recent focus has been given to nanopores as a potential DNA sequencing technology, for example as described by Clarke et al (2009. "Continuous base identification for single-molecule nanopore DNA sequencing". Nature Nanotechnology 4 (4): 265-270. doi: 10.1038/nnano.2009.12. PMID 19350039), incorporated herein by reference. When a potential is applied across a nanopore, there is a drop in the current flow when an analyte, such as a nucleotide, resides transiently in the barrel for a certain period of time. Nanopore detection of the nucleotide gives a current blockade of known signature and duration. The nucleotide content can then be determined by the number of blockade events, or the level of blockade as the nucleotide analyte passes through a single pore. This approach has been applied for determining other analytes, such as amino acid polymers, and for measuring stochastic interactions (See—Howorka et al. Stochastic detection of monovalent and bivalent protein-ligand interactions. *Angewandte Chemie International Edition* 43 (7), 842-846 (2004); and Cheley et al. A genetically encoded pore for the stochastic detection of a protein kinase. *ChemBioChem* 7 (12), 1923-1927 (2006) incorporated herein by reference.).

The completion of the first human genome sequencing in 2004, has spurred on the development of various new approaches aiming for sequencing a human genome in 15 minutes under $1000. Nanopore sequencing, which offers advantages of being label free, amplification free, long reading length, fast speed and low cost, is of particular interests for investigations [Venkatesan, 2011 NatNano]. Intensive studies have focused on lowering DNA translocation speed for resolving single bases. Recent progress showed that a processive enzyme ratchets DNA movement with single base resolution [Cherf, 2012 NatBiotech] and base identities can be sequentially read out (~28 ms median duration and ~40 pA maximum level separations) for sequencing [Manrao, 2012 NatBiotech]. With this speed, a minimum of $10^6$ parallel recordings are still needed to achieve 15 minutes human genome sequencing. However, fabricating electrodes/amplifiers array in high density is of technical challenges and is limiting both the throughput and cost of nanopore analysis technologies.

An aim of the present invention is to provide improved analyte analysis and detection using channel molecules, such as nanopores, and improved bilayer devices and methods for the analyte analysis.

DESCRIPTION OF THE INVENTION

According to a first aspect of the present invention, there is provided a method for detection of analyte interaction with a channel molecule held in a membrane, comprising the optical detection of a modification in the flux of a signal molecule as it passes through the channel molecule by the action of a membrane potential, wherein the modification in the flux is caused by at least partial blockage of the channel molecule by the analyte.

Advantageously, by using optical measurements of flux the present invention enables recordal of the flux through many channel molecules in parallel without the need for multiple complex and expensive arrays of electrodes. The optical measurements can mirror an electrical readout from multiple membrane channel molecules, but can be separated into multiple fluorescent traces for each channel. The method of the invention can replace electrical recording for applications that require high throughput screening such as a nanopore sequencing array.

The method may comprise forming the membrane, wherein the membrane contains the channel molecules. The membrane may be any material capable of supporting a functional channel molecule, such as a nanopore. The membrane may be a synthetic membrane, for example in embodiments of the invention wherein the channel molecules comprise solid-state nanopores. The membrane may comprise or consist of a polymer. The membrane may comprise or consist of block-copolymers, for example as provided in Discher, D. E. & Ahmed, F. Polymersomes. *Annu. Rev. Biomed. Eng.* 8, 323-341 (2006), incorporated herein by reference. The membrane may comprise or consist of a solid substrate layer, such as SiN. The membrane may comprise cross-linking lipids such as 23:2 Diyne PC [DC(8,9)PC] (1,2-bis(10,12-tricosadiynoyl)-sn-glycero-3-phosphocholine).

The membrane may comprise a bilayer, such as a bilayer of amphipathic molecules. The membrane may be synthetic. The membrane may be artificial. The bilayer may be artificial, for example non-natural. The bilayer may not be a cell bilayer. The bilayer may not be a patch clamp bilayer of a cell. The skilled person will understand that there are multiple methods for providing a bilayer. The bilayer may be provided by any artificial means of forming a bilayer. The bilayer may be provided by a droplet hydrogel bilayer (DHB) method, for example as provided in WO2009024775, the contents of which is incorporated herein by reference. The bilayer may be provided by a hydrogel-hydrogel interaction in a hydrophobic medium comprising amphipathic molecules, such as lipids. The bilayer may be provided by the bilayer array of the invention herein. Alternatively, other bilayer forming methods are available. For example, the bilayer may be provided by any one of the following techniques known to the skilled person comprising: patch clamping, for example optical patch clamping; black lipid membrane (BLM); otherwise known as painted BLM; Supported lipid bilayers (SLB); and tethered bilayer lipid membranes (t-BLM). The bilayer may be formed across an aperture in accordance with WO2008102121, the content of which is incorporated herein by reference. The bilayer may be formed at droplet to droplet interfaces in accordance with WO2014064444, the content of which is incorporated herein by reference.

The bilayer may comprise a Cis side and a Trans side. The channel molecules, such as αHL nanopores, may be placed on the Cis side of the bilayer and spontaneously insert into the bilayer and conduct the signal molecule, such as $Ca^{2+}$, from the Trans side of the bilayer into the Cis side.

The channel molecules may be provided in the bilayer by adding channel molecules to the bilayer after the bilayer is formed, or during formation of the bilayer. For example, the channel molecule may be provided in an aqueous suspension or solution in a hydrogel or droplet having a monolayer of amphipathic molecules, wherein the monolayer is brought into contact with an opposing monolayer to spontaneously form a bilayer, wherein the channel molecules may insert into the bilayer. Channel molecules may be provided to the bilayer by channel molecule-containing liposomes fusing with the bilayer.

A channel molecule may comprise a transmembrane pore. The channel molecules may comprise or consist of a nanopore. The channel molecule may be natural, for example derived from a biological organism, or the channel molecule may be synthetic. The channel molecule may be recombinantly produced. The channel molecule may be isolated from a membrane of a cell. The channel molecule may be a biological molecule. For example a pore-forming protein in a membrane such as a lipid bilayer.

The channel molecule may comprise alpha-hemolysin (α-HL). The channel molecule may comprise a modified alpha-hemolysin (α-HL), which is capable of enhanced detection of specific nucleotides in accordance with WO2010004273, the content of which is incorporated herein by reference. Alternatively, the channel molecule may comprise *Mycobacterium smegmatis* porin A (MspA). The channel molecule may comprise *Mycobacterium smegmatis* porin A (MspA) modified to improve translocation, for example by having neutral asparagine residues in place of three negatively charged aspartic acids. Phi29 polymerase may be used in conjunction with the channel molecule.

The MspA pore may be advantageous for DNA sequencing because of its shape and diameter. For example it has been shown to be tenfold more specific than αHL for identifying bases.

The channel may be a solid-state channel, for example comprising synthetic materials such as silicon nitride or graphene. A solid-state channel is typically a nanometer-sized hole formed in a synthetic membrane (usually SiNx or SiO2). The pore can be fabricated by focused ion or electron beams, allowing the size of the pore to be tuned. The channel may be a hybrid channel comprising a pore-forming protein set in synthetic material.

Multiple channels may be provided in the membrane. The number of channels provided in a single membrane may be controlled such that the channels are on average, distanced apart by 3 μm or more. For example, the channels may be provided at a density/concentration in the membrane such that single channels may be optically resolved. The maximum density of channels in the bilayer may be determined by the accuracy to which the point spread function corresponding to optical detection of the nanopore can be determined. For fluorescence based optical detection this accuracy may be about 1 nanometre, whereby the maximum density may be determined to be 1 channel molecule per square nanometre. The channel molecule may be provided at a concentration of at least one channel molecule per 2 nm×2 nm. The channel molecule may be provided at a concentration of at least one channel molecule per 5 nm×5 nm. The channel molecule may be provided at a concentration of at least one channel molecule per 10 nm×10 nm. The channel molecule may be provided at a concentration of at least one channel molecule per 50 nm×50 nm. The channel molecule may be provided at a concentration of at least one channel molecule per 100 nm×100 nm.

The concentration may be limited by the Raleigh diffraction limit for resolving individual channel molecule, for example in the absence of super-resolving the channel molecule position. For example channel molecule concentration may provide a channel molecule approximately every 200 nm×200 nm. The channel molecule may be provided at a concentration of at least one channel molecule per 300 nm×300 nm. The channel molecule may be provided at a concentration of at least one channel molecule per 400 nm×400 nm. The channel molecule may be provided at a concentration of at least one channel molecule per 500 nm×500 nm. The channel molecule may be provided at a concentration of at least one channel molecule per 1000 nm×1000 nm.

Advantageously, the present invention allows measurement of a very high density of channel molecules compared to conventional electrical methods for measuring signals from channel molecules.

The signal molecule may be a first signal-associated molecule provided on one side of the membrane, wherein the first signal-associated molecule is capable of flux through the channel molecule by the action of the membrane potential across the membrane;

and a second signal-associated molecule is provided on the opposing side of the membrane relative to the first signal-associated molecule, wherein the first and/or second signal associated molecules are arranged to emit an optical signal when in contact.

The signal molecule may only cause or provide optical detection after passing through the channel molecule. The signal molecule may interact with one or more other signal associated molecules to cause or provide optical emission for optical detection after passing through the channel molecule. For example, the signal molecule may interact with the second signal-associated molecule to cause or provide optical emission for optical detection after passing through the channel molecule. The optical emission may be provided upon laser excitation, for example at 473nm.

The signal molecule may be any molecule capable of providing an optically resolvable signal caused by the transit of the signal molecule through the channel molecule. For example, the signal molecule may be arranged to provide a change in refractive index of a material relative to the surroundings; or a change in optical absorption; or a change in fluorescence emission.

The signal molecule may be membrane-impermeant, such as bilayer-impermeant. The signal molecule may be an ion. The signal molecule may comprise electrolytes such as $Ca^{2+}$, $K^+$, $Na^+$ or, $Mg^{2+}$. The signal molecule may comprise $Ca^{2+}$.

The second signal-associated molecule may be membrane-impermeant, such as bilayer-impermeant. The second signal-associated molecule may comprise a dye. The second signal-associated molecule may comprise a fluorophore dye.

The second signal-associated molecule may comprise a calcium indicator. A calcium indicator is considered to be a molecule, such as a small molecule, that can chelate calcium ions. The second signal-associated molecule may comprise a calcium-specific aminopolycarboxylic acid. The second signal-associated molecule may comprise BAPTA (1,2-bis(o-aminophenoxy)ethane-N,N,N',N'-tetraacetic acid).

The second signal-associated molecule may comprise any molecule selected from the group comprising fura-2; indo-1; fluo-3; fluo-4; Calcium Green-1; Fluo-8; and Fluo-4; or combinations thereof. The second signal-associated molecule may comprise Fluo-8 or Fluo-4.

Advantageously, the binding of a $Ca^{2+}$ ion to a fluorescent indicator molecule leads to either an increase in quantum yield of fluorescence or emission/excitation wavelength shift that can be detected optically.

It will be understood by the skilled person that alternative signal molecules capable of flux through a channel molecule by the action of membrane potential may be envisaged.

In one embodiment of the invention, the signal molecule may be a quenching molecule. For example, an optical signal may be blocked during flux of the quencher, by action of the quencher on a fluorescing molecule that is capable of being quenched, wherein the blocking of the flux by the analyte causes less quenching signal molecules to pass through the channel molecule, thereby causing a detectable increase in the optical signal. Quenching signal molecules may comprise iodine ions, or nitroyl-quenchers.

Analyte interaction with a channel molecule may be analyte flux through the channel molecule. Analyte interaction with a channel molecule may be analyte insertion into the channel molecule. Analyte interaction with a channel molecule may be a blocking of the channel. Analyte interaction may be a change in conformation of the channel molecule. Analyte interaction with a channel molecule may be a stochastic blocking of the channel molecule. Analyte interaction with a channel molecule may be a specific blocking of the channel molecule, for example by an analyte having affinity for the channel molecule. The analyte may be a molecule capable of flux through the channel molecule under the action of a membrane potential. The analyte may be a molecule capable of at least insertion into the channel molecule under the action of a membrane potential. The analyte may be provided on only one side of the membrane.

The analyte may comprise or consist of a biological molecule. The analyte may comprise or consist of a peptide or nucleic acid. The analyte may comprise or consist of an oligomer, such as an oligonucleotide. The analyte may comprise or consist of a polynucleotide. The polynucleotide may comprise or consist of DNA. The polynucleotide may comprise or consist of RNA. The polynucleotide may be single stranded. The polynucleotide may be double stranded, at least in part.

The analyte may comprise an aptamer-protein complex. For example, a protein may be targeted by an aptamer specific for that protein, wherein the aptamer interacts with the channel molecule to provide a characteristic modification in flux, thereby identifying the protein.

In an embodiment where the nucleic acid is at least partially double stranded nucleic acid, the action of flux through the channel molecule may unzip the double stranded nucleic acid to become single stranded.

The method for detection of analyte interaction with a channel molecule held in a membrane may be a method for optical screening of a polynucleotide present in one or more samples, wherein the analyte is a polynucleotide. The polynucleotide analyte may comprise a template polynucleotide arranged to hybridise with a target polynucleotide in the sample(s). The template polynucleotide may comprise a complementary target sequence, which is intended to be complementary relative to a target polynucleotide sequence potentially in the sample(s). The complementary target sequence may be known/pre-determined. The template polynucleotide may further comprise 5' and 3' single stranded tag sequences, which flank the complementary target sequence. The tag sequences may not be arranged to hybridise with any polynucleotide in the sample.

A reduction in the flux of the signal molecule may be indicative of a successful hybridisation with the template polynucleotide as the hybridised double stranded polynucleotide at least partially blocks the channel molecule. Modification of flux may be detected as the hybridised template and sample polynucleotide is unzipped as it passes through the channel molecule. The template polynucleotide and sample derived target polynucleotide may be hybridized prior to introduction to the membrane, such as the bilayer. The template polynucleotide may comprise a specific nucleotide sequence known to provide a specific signal during interaction with the channel molecule. The optically detected reduction/blockage of flux through the channel molecule may be due to the presence of a specific nucleotide sequence entering the channel/pore of the channel molecule. The specific nucleotide sequence may be a reporter sequence.

Advantageously, with up to ~300 Hz frame rate and ~1 pA amplitude resolution, the method of optical screening could resolve fast kinetic process like miRNA unzipping in nanopores. miRNA, a short (~22 nucleotides) and non-coding RNA fragment, is of significant biological importance but difficult to be quantitatively analyzed by PCR based methods. The miRNA, when hybridized with a DNA probe and electrically stretched in a nanopore, can be forced to unzip. The unzipping kinetics, which can be recorded from a single pore in the membrane may reveal the miRNA identity statistically [Wang, 2011 Nature Nano]. The unzipping duration time is widely distributed and may requires a significant amount of events for statistics. The method of the invention which is capable of imaging channel molecule activities in massive throughput and streams of single molecule fluorescent traces simultaneously, is ideal for ultra fast recording and screening of miRNA samples.

The method of optical screening may comprise the simultaneous or parallel screening of multiple samples and/or may comprise the use of multiple template polynucleotides. The method for optical screening may be carried out in an array of membranes. For example, the method of optical screening may comprise the use of the bilayer array according to invention herein, wherein the bilayer array comprises an array of bilayers comprising the channel molecules held in the bilayers. The same template polynucleotide sequence may be provided on two or more, or each, membrane of the array. Alternatively or additionally, the same sample polynucleotides may be provided on two or more, or each, membrane of the array. A different template polynucleotide sequence may be provided on two or more, or each, membrane of the array. Different sample polynucleotides may be provided on two or more, or each, membranes of the array.

The sample may be, for example, a sample of blood, urine, serum, saliva, cells or tissue. The sample may be an environmental sample. The sample may comprise any medium potentially comprising polynucleotide sequences of interest.

The target polynucleotide in the sample may comprise DNA, RNA, mRNA, or miRNA, such as siRNA. The target polynucleotide in the sample may be less than 100 nucleotides. The target polynucleotide in the sample may be less than 50 nucleotides. The target polynucleotide in the sample may be less than 30 nucleotides. The target polynucleotide in the sample may be less than 25 nucleotides. The target polynucleotide in the sample may be between about 8 nucleotides and about 50 nucleotides, or between about 8 nucleotides and about 30 nucleotides.

The method for detection of analyte interaction with a channel molecule held in a membrane may be a method for optical polymer sequencing. The method for detection of analyte interaction with a channel molecule held in a membrane may be a method for optical polynucleotide sequencing. The optical sequencing may be parallel, such as massively parallel, sequencing in an array.

The modification in the flux may be caused by blockage of the channel molecule by the polynucleotide bases as they pass through the channel molecule. Different bases may be distinguishable by different levels of flux blockage or interference, which can be correlated to individual bases. For example, bases A, C, G and T may occupy a different space relative to each other and thereby block the channel molecule by varying degrees.

The optical polynucleotide sequencing may not require the use of labels, such as fluorescent labels tagged to the polynucleotide, or oligonucleotides arranged to hybridise to the polynucleotide to be sequenced. However method of the invention may be used in channel molecule mediated polynucleotide sequencing techniques, which require optical measurement of fluorescently labelled probes, for example as described in McNally B, Singer A, Yu Z, Sun Y, Weng Z, Meller A (2010). "Optical recognition of converted DNA nucleotides for single molecule DNA sequencing using nanopore arrays." Nano Lett. 10 (6): 2237-2244, incorporated herein by reference.

The optical polynucleotide sequencing may comprise the use of the methods described by Clarke et al (2009. "Continuous base identification for single-molecule nanopore DNA sequencing". Nature Nanotechnology 4 (4): 265-270. doi:10.1038/nnano.2009.12. PMID 19350039), with optical detection of the signal molecule flux.

The polynucleotide analyte may be double stranded, wherein the polynucleotide is unzipped as it passes through the channel molecule. Double stranded polynucleotides may comprise a hairpin loop to link sense and antisense strands. The hairpin loop may be added to a double stranded polynucleotide prior to sequencing. The optical polynucleotide sequencing may comprise the use of the hairpin loop method for double stranded polynucleotide sequencing using the channel in accordance with WO2013014451, the content of which is incorporated herein by reference, whereby the method is modified to provide optical detection of flux through the channel in accordance with the invention herein.

The membrane potential may be provided. The membrane potential may be applied across the membrane such that the signal molecule, for example the first signal-associated molecule, is transported through the channel molecule and interacts with the second signal-associated molecule to emit an optical signal.

The membrane potential may be provide by electrical means, or chemical means. The membrane potential may be ionic membrane potential. The membrane potential may be a chemical membrane potential, such as an osmotic membrane potential. Electrodes may be applied to provide membrane potential. For example a cathode and anode may be applied to provide the membrane potential. A cathode may be applied to one side of the membrane and an opposing anode may be applied to the opposite side of the membrane. A single set of electrodes, that is a cathode and an anode, may be applied. The method may not comprise the use of multiple sets of electrodes. In an embodiment comprising an array of membranes, a single means of providing the membrane potential may apply the membrane potential for all membranes in the array, or groups of membranes in the array. The array of membranes may be served by a common electrode or share a common buffer to provide a chemical membrane potential. For example in a bilayer array provided by multiple hydrogel pillars opposing a hydrogel surface, the discrete bilayers may be formed therebetween, and all hydrogel pillars may be electrically or chemically connected through the hydrogel.

The skilled person will understand that there many methods of setting up a membrane potential across a membrane and such methods may be applied in the present invention.

The emitted optical signal may be detected. Any modification or lack thereof, in the optical signal may be detected as the flux of the signal molecule is modified by at least partial blocking of the channel molecule by the analyte as it interacts with the channel molecule.

Optical detection may comprise microscopy or spectroscopy of the membrane and membrane region. Optical detection may comprise the use of Total Internal Reflection Fluorescence (TIRF). Optical detection may comprise the use of HiLo microscopy, for example as provided by Tokunaga et al (2008. Highly inclined thin illumination enables clear single-molecule imaging in cells. Nat Meth 5, 159-161). Optical detection may comprise the use of other glancing-incidence illumination techniques. Any suitable optical detection means may be used to detect optical signals/emission in the membrane region immediately surrounding the membrane and channel molecules of the membrane. Optical detection may comprise the use of surface plasmon resonance. Optical detection may comprise the use of super-resolution microscopy, such as deterministic super-resolution, including STED, GSD, RESOLFT or SSIM; or stochastical super-resolution, including SOFI, or single-molecule localization methods (SMLM) such as SPDM, SPDMphymod, PALM, FPALM, STORM or dSTORM. Optical detection may comprise the use of epifluorescence microscopy, confocal laser scanning microscopy (LSM), or total internal reflection fluorescence (TIRF) microscopy. Optical detection may comprise the use of fluorescence correlation spectroscopy (FCS). Image correlation spectroscopy (ICS) may be used to calculate the spatial correlation function of the fluctuations in fluorescence intensity of an image, which can be acquired by confocal or two-photon LSM or with TIRF microscopy. Optical detection techniques may be described in Ana J. García-Sáez, Petra Schwille. Surface analysis of membrane dynamics Biochimica et Biophysica Acta 1798 (2010) 766-776, the content of which is incorporated by reference.

The method may comprise the detection of analyte interaction with multiple channel molecules held in a membrane. The method may comprise the detection of analyte interaction with multiple channel molecules held in multiple membranes. The method may comprise the detection of analyte interaction with one or more separate channel molecules held in multiple membranes.

The method may comprise the detection of analyte interaction with multiple channel molecules held in an array of membranes. The optical field of the optical detection means may be capable of encompassing and detecting optical signals/emissions across an array of membranes and channel molecules.

In an embodiment comprising the detection of analyte interaction with multiple channel molecules held in multiple membranes, such as an array of membranes, the membrane potential may be provide by a single means. For example a single set of electrodes may be applied to provide the membrane potential for all membranes. For example, all membranes in an array may be provided with a single cathode and single anode for providing membrane potential. In an embodiment comprising the detection of analyte interaction with multiple channel molecules held in multiple membranes, such as an array of membranes, the membrane potential may not be provide by multiple sets of electrodes, for example multiple cathodes or anodes.

Advantageously, the invention can be applied without the need for multiple electrode connections, which is a major issue holding back the feasibility of high-throughput methods using channel molecules, membranes and optical detections means. The present invention overcomes such an issue by the ability to apply a single pair of electrodes which act upon all, or groups of, membranes in the method, leading to a breakthrough in the ability to provide high-throughput methodologies to optical channel molecule detection technology.

The optical detection may be recorded by a charge-coupled device (CCD) camera. The optical detection may be recorded by an electron multiplying CCD camera. Up to, and over, 2500 pores may be recorded simultaneously with an Electron Multiplying CCD camera (ixon3, Andor).

The term "at least partial blockage" of the channel molecule may be considered to be the reduction of flux of the signal molecule through the channel molecule due to the bulk of the analyte molecule. The blockage may be complete blockage such that no flux of the signal molecule can occur in the presence of the analyte in the channel molecule. Partial blockage may allow for some signal molecules to pass through the channel molecule.

The term "flux" may be considered to be the passage of a molecule from one side of a membrane to the other side of the membrane through a channel molecule.

The term "optical signal" or "optical emission" may be considered to be the emission of an energy, such as a wavelength, capable of being detected optically. For example fluorescence and light may be optical signals/emissions.

According to another aspect of the invention, there is provided a bilayer array comprising:
  opposing hydrogel surfaces provided by a first component comprising an array of discrete hydrogel surfaces opposing a hydrogel surface of a second component;
  wherein the opposing hydrogel surfaces are immersed in a hydrophobic medium comprising amphipathic molecules, and wherein the opposing hydrogel surfaces are spaced apart sufficiently to provide bilayers of the amphipathic molecules formed therebetween;
  channel molecules in the bilayers;
  a means arranged to provide a membrane potential across the bilayers.

The bilayer array of the present invention provides improvements over the known bilayer methods, such as droplet-hydrogel bilayers (DHBs) and can be used with the method of the invention herein. A DHB is a low cost, simple and convenient system for basic biological sensing with optical recording. However, a single large DHB (~1 mm$^2$) may lead to an unstable bilayer at high potentials, which can limit the scalability of the system. Besides that, only one type of analyte may be measured in a single DHB at a time, which prohibits its application of biological screening unless a highly parallel array of droplets and electrodes are used simultaneously. On the contrary, the present invention can be provided in the format of a miniaturized, chip shaped and portable device containing a massive array of small but durable bilayers, which is more ideal for biological sensing in ultra large throughput. This chip device can be made of ion conductive hydrogel materials, which electrically connects all the bilayer with one pair of common electrodes to drive ion flux for optical recording. The bilayer array can localize biological samples in position and each bilayer compartment requires only a minimum amount of precious biological samples for high throughput screening.

The bilayer array may be used in the method for detection of analyte interaction with a channel molecule held in a bilayer, according to the invention herein.

The array of hydrogel surfaces may be provided on an array of pillars extending from the first component. The first component may comprise an array of pillars. The pillars may comprise and/or be formed of a hydrogel. The apex/top surface of the pillars may form the hydrogel surface for forming the bilayer.

The pillars may be substantially square in cross-section. The pillars may not be circular in cross section.

A discrete hydrogel surface of the first component may be less than about 200 microns in diameter. A discrete hydrogel surface of the first component may be about 100 microns in diameter, or less. A discrete hydrogel surface of the first component may be about 50 microns in diameter, or less. A discrete hydrogel surface of the first component may be about 20 microns in diameter, or less. A discrete hydrogel surface of the first component may be less than about 40 mm$^2$ in surface area. A discrete hydrogel surface of the first component may be about 10 mm$^2$ in surface area, or less. A discrete hydrogel surface of the first component may be about 2.5 mm$^2$ in surface area, or less. A discrete hydrogel surface of the first component may be about 0.4 mm$^2$ in surface area, or less. Reference to the diameter or area of a discrete hydrogel surface of the first component may refer to each hydrogel surface of the array of hydrogel surfaces.

The total bilayer area provided by the array of bilayers may be at least 1 mm$^2$. The total bilayer area provided by the array of bilayers may be at least 2 mm$^2$, at least 5 mm$^2$, at least 10 mm$^2$, at least 15 mm$^2$, at least 20 mm$^2$, or at least 25 mm$^2$.

The array of discrete hydrogel surfaces of the first component may be arranged in an array of rows and columns, for example a grid arrangement. The array may comprise at least 2 discrete hydrogel surfaces. The array may comprise at least 4 discrete hydrogel surfaces. The array may comprise at least 10 discrete hydrogel surfaces. The array may comprise at least 25 discrete hydrogel surfaces. The array may comprise at least 100 discrete hydrogel surfaces. The array may comprise between about 2 and about 1000 discrete hydrogel surfaces. The array may comprise between about 2 and about 2500 discrete hydrogel surfaces. The array may comprise between about 4 and about 2500 discrete hydrogel surfaces.

The bilayers may be arranged in an array of rows and columns, for example a grid arrangement. The bilayer array may comprise at least 10 discrete bilayers. The bilayer array may comprise at least 50 discrete bilayers. The bilayer array may comprise at least 100 discrete bilayers. The bilayer array may comprise at least 200 discrete bilayers. The bilayer array may comprise at least 300 discrete bilayers. The bilayer array may comprise at least 500 discrete bilayers. The bilayer array may comprise at least 1000 discrete bilayers. The bilayer array may comprise at least 1500 discrete bilayers. The bilayer array may comprise at least 2500 discrete bilayers. The bilayer array may comprise between about 10 and about 3000 discrete bilayers. The bilayer array may comprise between about 50 and about 10000 discrete bilayers. The bilayer array may comprise between about 50 and about $10^6$ discrete bilayers. The bilayer array may comprise between about 1000 and about $10^6$ discrete bilayers.

The first component may comprise or consist of a hydrogel. The first component comprising an array of hydrogel surfaces may be a single cast of hydrogel.

The first component comprising an array of hydrogel surfaces may further comprise a barrier material arranged to prevent cross-contamination of reagents and/or channel molecules between adjacent hydrogel surfaces. The barrier material may be arranged between the hydrogel surfaces, for example between the pillars. The barrier material may be a solid. The barrier material may be solid and rigid. The barrier material may be transparent. The barrier material may be liquid impermeable. The barrier material may be non-porous. The barrier material may comprise or consist of a plastic polymer, such as poly(methyl methacrylate (PMMA). The barrier material may comprise or consist of any suitable material that can prevent translocation of chemical reagents, such as small molecules (e.g. fluorophores) and/or biological molecules, such as nucleic acid, peptides, or proteins (e.g. channel molecules or analytes). The barrier material may comprise or consist of non-conducting material. The barrier material may comprise materials selected from the group comprising PTFE; hydrophilic-treated PDMS; silica; glass; diamond; and acetal resin (Delrin™); or combinations thereof.

The first component may be circular in shape. The first component may be a disc shape. The first component may be sized to fit onto a standard microscope slide. The first component may be about 4-16 mm in diameter, such as about 8 mm in diameter. The first component may be between about 100 and about 1000 microns in thickness.

The first component may be supported by a plate. For example the first component may be in the form of a hydrogel on a backing plate. The plate may be a rigid solid. The plate may be transparent. The plate may be glass, such as a glass coverslip. The plate may be between about 80 and about 170 microns in thickness, or less. The plate may be positioned on the surface of the first component opposite the hydrogel/bilayer-forming surfaces.

Advantageously, providing the first component with a plate can facilitate manipulation of a potentially weak and thin hydrogel based first component. For example tweezers may be used to manipulate the first component during assembly of the bilayer array. The plate may also benefit the casting of a smooth, flat/planar surface on the first component.

The second component may comprise hydrogel, such as hydrogel layer. The second component may comprise a planar hydrogel layer.

The second component may be sized to substantially match the size of the first component. The second component may be at least 4 mm in diameter, or about 8 mm in diameter. The second component may be about 5-100 mm$^2$ in size. The second component may be capable of supporting an array of at least 4 bilayers, at least 10 bilayers, or at least 50 bilayers. The second component may be about 0.1 microns in thickness. The second component may be less than about 10000 microns in thickness. The second component may be between about 0.01 and about 10000 microns in thickness.

The second component may comprise a plate. The hydrogel of the second component may be supported on a plate. For example the second component may be in the form of a hydrogel layered on a plate. The plate may be a rigid solid. The plate may be transparent. The plate may be glass, such as a glass coverslip. The plate may be between 80 and about 1000 microns in thickness, or less. The combined thickness of the second component with the plate may be less than about 150 microns.

The means for providing a membrane potential may comprise cathode and anode electrodes. The cathode and anode electrodes may be arranged on opposing components, on either side of the bilayer in order to provide a membrane potential across the bilayer. The bilayer array may comprise only a single set of anodes and cathodes for providing membrane potential across all the bilayers in the array. For example, each separate bilayer may not comprise a separate electrode connection. A cathode may connect to the first component, and an opposing anode may connect to the second component; or vice versa.

The hydrogel may comprise or consist of hydrophilic material. The hydrogel may comprise or consist of hydrophilic polymer. The hydrogel may comprise or consist of substantially transparent hydrophilic polymer. The hydrogel may comprise or consist of agarose. Other hydrogel materials may be suitable, such as polyacrylamide, cross-linked polyethylene glycol, or nitro-cellulose.

The hydrogel may comprise or consist of less than 5% (w/v) agarose. The hydrogel may comprise or consist of less than 4% (w/v) agarose. The hydrogel may comprise or consist of about 3% (w/v) agarose. The hydrogel may comprise or consist of greater than 1% (w/v) agarose. The hydrogel may comprise or consist of 2% (w/v) agarose, or more. The hydrogel may comprise or consist of between about 2% and about 4% agarose. The hydrogel may comprise or consist of between about 2.5% (w/v) and about 3.5% (w/v) agarose.

The amphipathic molecules may comprise or consist of lipid. The bilayer may comprise or consist of amphipathic molecules, such as lipids. The bilayer may be a lipid-bilayer. The amphipathic molecules used in any method of the invention may be lipid molecules, in particular, surfactant molecules may be used. The lipid molecules may be selected from the group comprising fatty acyls, glycerolipids, glycerophospholipids, sphingolipids, sterol lipids, prenollipids, saccharolipids, polyketides, phospholipids, glycolipids and cholesterol.

The lipid may include any of the group comprising monoolein; 1,2-dioleoyl-sn-glycero-S-phosphocholine (DOPC); 1,2-diphytanoyl-sn-glycero-3-phosphatidylcholine (DPhPC); palmitoyl oleoyl phosphatidylcholine (POPC); 1-palmitoyl-2-oleoyl-phosphatidylethanolamine (POPE); 1-palmitoyl-2-oleoyl-phosphatidylethanolamine; and 1-palmitoyl-2-oleoylphosphatidylglycerol (POPE/POPG) mixtures; or mixtures thereof.

The hydrophobic medium may comprise oil. The hydrophobic medium comprising amphipathic molecules may comprise or consist of lipid-in-oil. The oil may be a hydrocarbon, which may be branched or unbranched, and may be substituted or unsubstituted. For example, the hydrocarbon may have from 5 to 20 carbon atoms, more preferably from 10 to 17 carbon atoms. Suitable oils include alkanes or alkenes, such as hexadecane, decane, pentane or squalene, or fluorinated oils, or silicone based oils, or carbon tetrachloride; or mixtures thereof. In one embodiment the oil is an n-alkane, such as a C10 to C17 n-alkane, e.g. n-hexadecane (C16). The oil may comprise a 1:1 (v:v) mixture of hexadecane and silicone oil AR20 (Sigma-Aldrich).

In an embodiment comprising the use of a lipid-in-oil, the lipid-in-oil solution may comprise from about 1 mg/ml to about 30 mg/ml of lipid in the oil. The lipid-in-oil solution may comprise about 5 mg/ml of lipid.

The lipid may comprise a phospholipid, such as a phosphocholine lipid, e.g. 1,2-diphytanoyl-sn-glycero-3-phophocholine (DPhPC).

The composition of the hydrogel may be controlled to contain the correct salts to allow an electrical current to be carried, for example, NaCl, KCl, $MgCl_2$ and/or other salts may be included. The hydrogel may also comprise common buffering agents to control pH, for example, Bis-tris, Tris, Hepes, sodium phosphate and/or potassium phosphate. The hydrogel of the first component may comprise a different composition to the hydrogel of the second component. For example, the bilayer may comprise a cis side and a trans side, wherein an appropriate composition is provided on either side of the bilayer. The first component hydrogel may comprise a potassium chloride buffer (for example, 1.5 M KCl, 10 mM HEPES, PH 7.0) and the second component hydrogel may comprise a calcium chloride buffer (for example, 0.75 M $CaCl_2$, 10 mM HEPES, PH 7.0). The buffer, for example on the cis side of the bilayer, may further comprise Ethylenediaminetetraacetic acid (EDTA) for competitive binding of the ion, such as $Ca^{2+}$, whereby fluorescence diminishes when away from the centre of the channel due to the competitive binding.

Salts may also be included for other reasons, for example, to stabilise proteins, to control binding components, to control the osmotic gradient across the bilayer and/or to activate fluorescent probes.

According to another aspect of the present invention, there is provided a method of manufacturing a bilayer array comprising providing a mould for casting a hydrogel first component, wherein the mould comprises an array of cavities for forming the hydrogel first component with an array of hydrogel pillars;

pouring a liquid arranged to set into a hydrogel into the mould;

laying a plate onto the surface of the liquid and setting the liquid to form the hydrogel first component;

removing the mould from the hydrogel first component;

optionally coating a barrier material on the hydrogel first component, between the hydrogel pillars;

adding a reagents and/or samples to one or more hydrogel pillars;

providing a second component comprising a hydrogel surface on a plate;

submerging the hydrogel surfaces of the first and second components in a volume of hydrophobic medium comprising amphipathic molecules, thereby forming a monolayer of amphipathic molecules on the hydrogel surfaces of the first and second components;

bringing the first and second components into an opposing position relative to each other such that the monolayers of amphipathic molecules form a bilayer.

According to another aspect of the present invention, there is provided a bilayer array formed by the method of the invention herein.

According to another aspect of the present invention, there is provided a method of manufacturing a component for a bilayer array comprising:

providing a mould for casting a hydrogel component, wherein the mould comprises an array of cavities for casting a hydrogel component comprising an array of pillars;

pouring a liquid arranged to set into a hydrogel into the mould;

laying a plate onto the surface of the liquid and setting the liquid to form a hydrogel component;

removing the mould from the hydrogel component.

The method of manufacture may further comprise coating a barrier material onto the hydrogel component, between the pillars.

The array of cavities of the mould may be arranged in an array. The cavities may be arrayed in rows and columns. The array of cavities may be arranged in a grid.

Coating the barrier material on the hydrogel first component may comprise spinning the coating in a liquid form, and allowing the liquid form of the barrier material to set.

The mould may be etched by photolithography. The mould may be etched from a photoresist material, for example SU-8 or similar.

According to another aspect of the present invention, there is provided a component for a bilayer array formed by the method of the invention herein.

According to another aspect of the present invention, there is provided a hydrogel component for a bilayer array comprising an array of pillars extending from the surface of the hydrogel component, and a barrier material coating the surface of the component between the pillars.

According to another aspect of the present invention, there is provided a kit for forming a bilayer array comprising:

a first component comprising an array of discrete hydrogel surfaces; and a second component comprising a hydrogel layer.

The kit may further comprise a volume of hydrophobic medium comprising amphipathic molecules. The kit may further comprise a cathode and anode. The kit may further comprise channel molecules. The kit may further comprise reagents. The kit may further comprise one or more buffers.

According to another aspect of the present invention, there is provided a kit for manufacturing a bilayer array comprising:

a first mould for casting a first component comprising an array of discrete hydrogel surfaces; and a second mould for casting a second component comprising a hydrogel layer.

The kit(s) of the invention may further comprise instructions for manufacture and/or assembly and/or use of the bilayer array.

The kit for manufacturing a bilayer array may comprise a hydrogel material in liquid form. The kit for manufacturing a bilayer array may comprise a hydrogel material in a powder or granular form, which is capable of being reconstituted in an aqueous medium. The kit for manufacturing a bilayer array may comprise a hydrogel material in a solid or gel solid form, which can be melted/liquified for casting into the mould. The kit for manufacturing a bilayer array may comprise a barrier material. The kit for manufacturing a bilayer array may further comprise a volume of hydrophobic medium comprising amphipathic molecules.

The kit for manufacturing a bilayer array may comprise a cathode and anode. The kit for manufacturing a bilayer array may comprise channel molecules. The kit for manufacturing a bilayer array may comprise reagents. The kit for manufacturing a bilayer array may comprise one or more buffers.

According to another aspect of the present invention, there is provided a method of optical screening of a polynucleotide present in one or more samples, the method comprising the steps:
providing a membrane comprising channel molecules held in the membrane;
providing one or more template polynucleotides and one or more polynucleotides from one or more samples on one side of the membrane;
providing a membrane potential across the membrane, such that it provides flux of a signal molecule through the channel molecules;
detecting hybridisation, or lack thereof, of the one or more template polynucleotides with polynucleotide in the one or more samples by optically detecting any modification in flux of the signal molecule through the channel molecules.

The method of optical screening may comprise the simultaneous or parallel screening of multiple samples and/or may comprise the use of multiple template nucleotides. For example, the method of optical screening may comprise the use of the bilayer array according to invention, wherein the bilayer array comprises an array of bilayers comprising the channel molecules held in the bilayers. The one or more template polynucleotides may be deposited on the one or more hydrogel surfaces of the first component, and the polynucleotides from one or more samples may be deposited on the one or more hydrogel surfaces of the first component.

The same template nucleic acid sequence may be provided on two or more, or each, hydrogel surfaces of the first component. The same sample nucleic acids may be provided on two or more, or each, hydrogel surfaces of the first component. A different template nucleic acid sequence may be provided on two or more, or each, hydrogel surfaces of the first component. Different sample nucleic acids may be provided on two or more, or each, hydrogel surfaces of the first component.

According to another aspect of the present invention, there is provided the use of the bilayer array of the invention herein, for optical sequencing, and optionally wherein the optical sequencing is parallel sequencing in an array.

According to another aspect of the present invention, there is provided the use of the bilayer array of the invention herein, for analyte analysis, and optionally wherein the analyte analysis is parallel sequencing in an array.

According to another aspect of the invention, there is provided a method for detection of analyte interaction with a nanopore held in a bilayer of amphipathic molecules, comprising:
providing a bilayer of amphipathic molecules, wherein the bilayer comprises one or more nanopores;
providing a first signal-associated molecule on one side of the bilayer, wherein the first signal-associated molecule is capable of flux through the nanopore(s) by the action of a membrane potential across the bilayer;
providing a second signal-associated molecule on the opposing side of the bilayer relative to the first signal-associated molecule, wherein the first and/or second signal associated molecules are arranged to emit an optical signal when in contact;
providing an analyte on at least one side of the bilayer;
applying a membrane potential across the bilayer such that the first signal-associated molecule is transported through the nanopore and interacts with the second signal-associated molecule to emit an optical signal;
detecting the optical signal; and
detecting any modification, or lack thereof, in the optical signal as the flux of the first signal-associated molecule is modified by at least partial blocking of the nanopore by the analyte as it interacts with the nanopore.

The method of the invention herein, and/or the bilayer array of the invention may be manipulated or implemented by a robotic system. For example, the deposition of sample, analyte, channel molecules and/or other reagents onto the hydrogel, or into the region of the membrane may be carried out by robot spotting, or robot pipetting. A droplet of sample, analyte, channel molecules and/or other reagents may be provided to the robot, which may spot the sample, analyte, channel molecules and/or other reagents in the bilayer array. Once the first component and second component of the bilayer array is formed, the use of the bilayer array may be fully or partially automated.

Advantageously, the use of an automated robot is made possible by a bilayer array of the present invention which allows individual spots of sample, analyte, channel molecules and/or other reagents to be deposited on the discrete hydrogel surfaces prior to forming the bilayers. Automated robot manipulation greatly enhances the use of the method of the invention and the bilayer array of the invention for high-throughput screening, analysis and sequencing.

The skilled person will understand that optional features of one embodiment or aspect of the invention may be applicable, where appropriate, to other embodiments or aspects of the invention.

Embodiments of the invention will now be described in more detail, by way of example only, with reference to the accompanying drawings.

Figure 5:
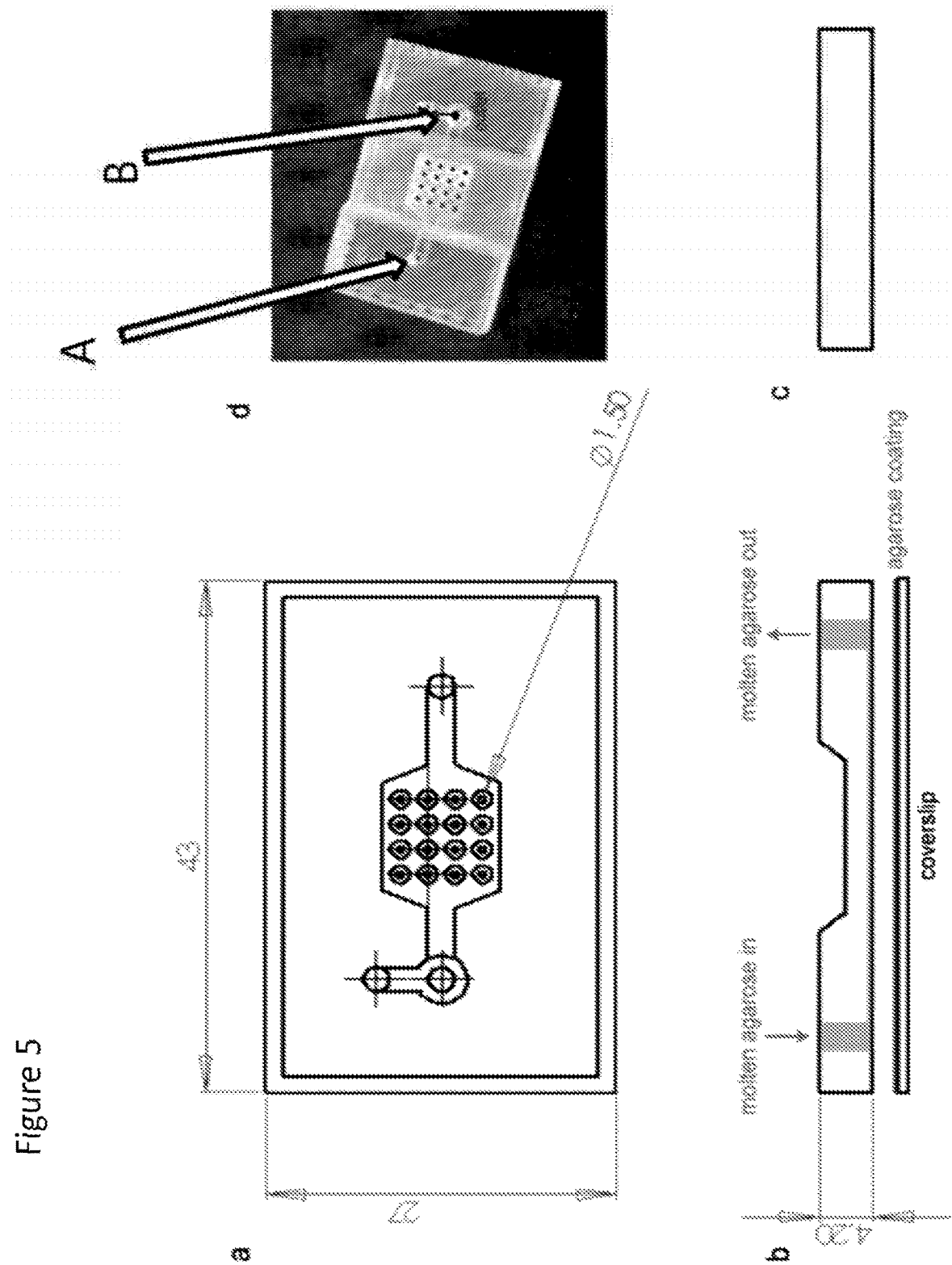

FIG. 1|Evaluating the amplitude resolution of optical single channel recording by static DNA blockages in DHB. a, The diagram of a single DHB in the 16 well measurement device (FIG. 5). A 60× TIRF objective is used both for TIRF illumination and image recording. Voltage protocols are applied with a pair of Ag/AgCl electrodes as illustrated in the figure. Agarose is coated on the ground electrode to facilitate electrode stabbing into the droplet. b, The diagram of the area near the bilayer. Free αHL in the droplet spontaneously inserts into the DHB. At +100 mV, the area near an inserted αHL shows strong fluorescence when $Ca^{2+}$ is driven through the nanopore and bind with Fluo-8. At this potential, streptavidine (square) tethered ssDNA (line/curves) is also electrically driven into the pore, which blocks the $Ca^{2+}$ flow and reduces the fluorescence. c, The fluorescent trace of a representative DNA blockage cycle. The trace amplitude is normalized so that the mean intensities of (III) and (IV) are 0 and 1. The normalized fluorescent amplitude of (II) identifies the DNA being captured. d, A frame containing fluorescent spots representing open (circles A) and blocked nanopores (circles B) to show the throughput of parallel recording. Scale bar: 10 μm. e, A continuous trace of nanopore blockages with a mixture of 2 types of DNA ($X_5$, cyan, histogram level 3; $C_{40}$, blue, histogram level 4). Level 6 in the histogram is due to the gating of αHL at negative potential. f, The correlation between optical recording (Table 2) and patch clamp electrical recording (Table 3) for different DNA blockage activities. FIG. 1 discloses SEQ ID NOS 9-11, respectively, in order of appearance.

Figure 2:
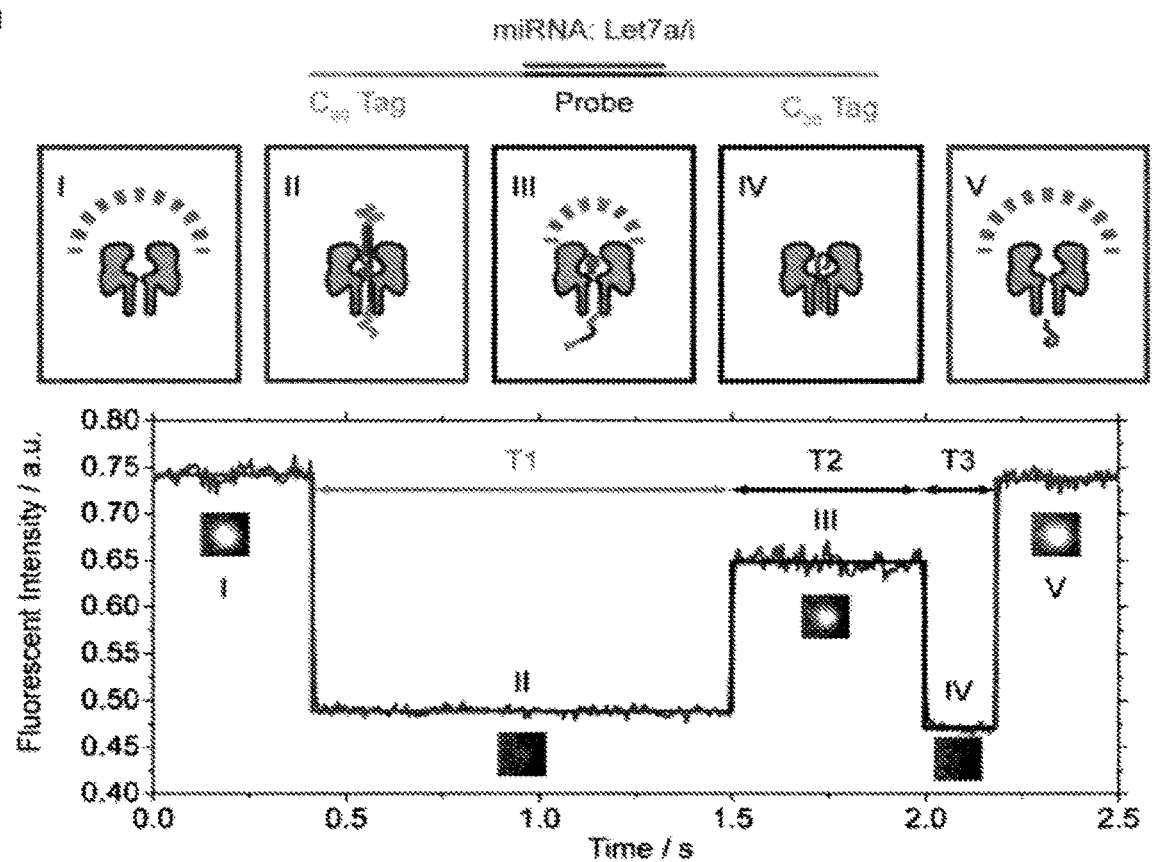
Figure 2:
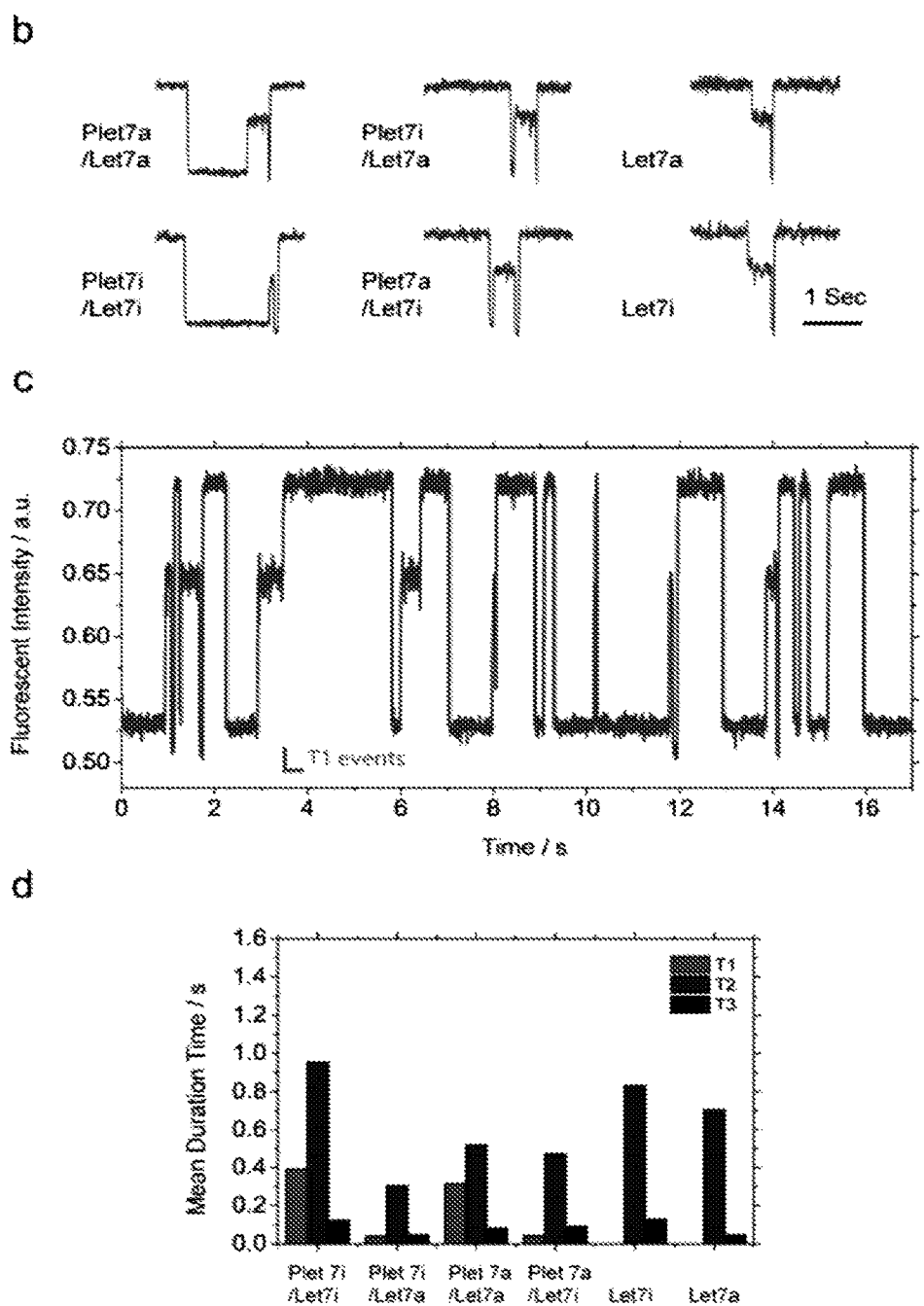
Figure 2:
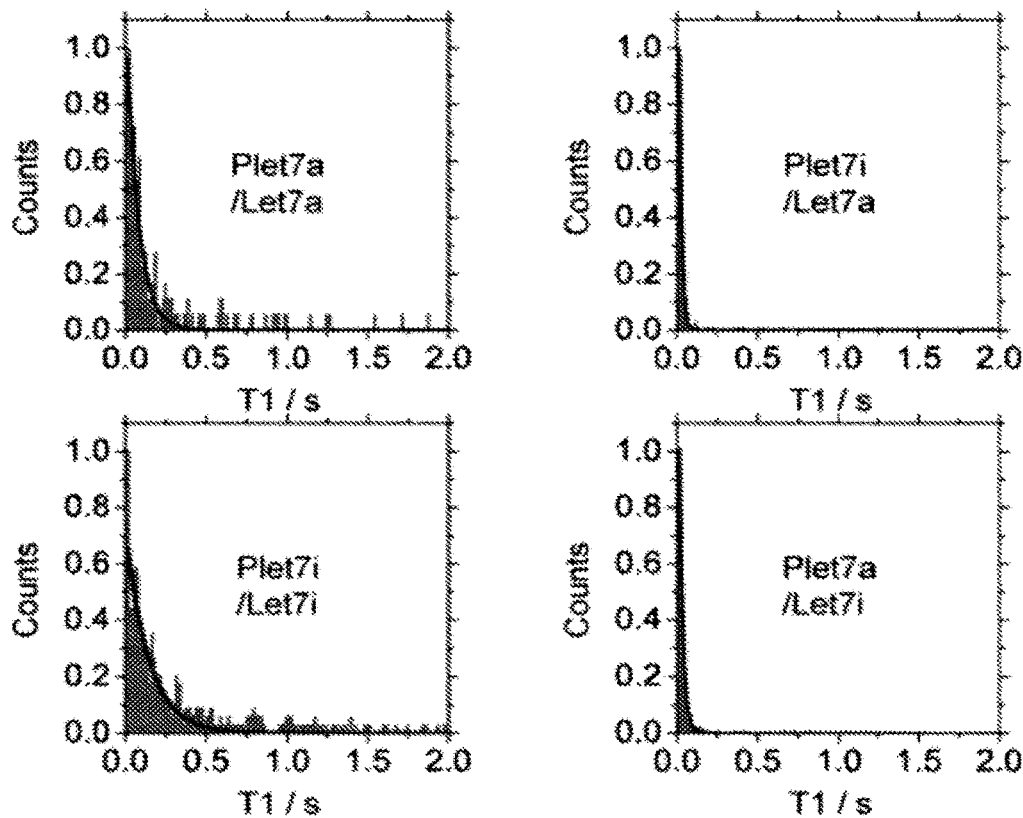

FIG. 2|Demonstrating the time resolution of optical single channel recording by kinetic miRNA unzipping in DHB. a, A representative miRNA unzipping event in the nanopore with optical recording. The miRNA is hybridized with the DNA probe. Poly-C ssDNA tags (SEQ ID NO: 1) on both ends of the probe are designed to initiate unzipping. At +160 mV, an open nanopore (I) shows strong fluorescence and then the hybridized nucleic acid complex is captured to unzip in the pore (II). Upon finishing unzipping, the DNA probe has translocated through the pore and the miRNA is left behind in the vestibule (III). Then the miRNA translocates through the pore (IV) and the pore re-opens (V) for the next event. b, Characteristic events for different probe/miRNA combinations and the miRNA controls. Matched/Un-matched miRNA to the probe normally generates long/short T1 events while miRNA translocation doesn't show T1 event at all. c, A continuous fluorescent trace of miRNA (Plet7a/Let7a) unzipping at +160 mV. Magenta fitting lines highlight the T1 events. d, The statistics of mean duration time for different probe/miRNA combinations and the miRNA controls. The matched probe/miRNA shows significantly longer T1 than the unmatched counterpart, which further confirms that T1 is hybridization strength dependent. e, The histogram of T1 for all the probe/miRNA combinations. The distribution follows an exponential fitting and the fitted rate constant reflects the hybridization strength (Supplementary Discussion 4).

Figure 3:
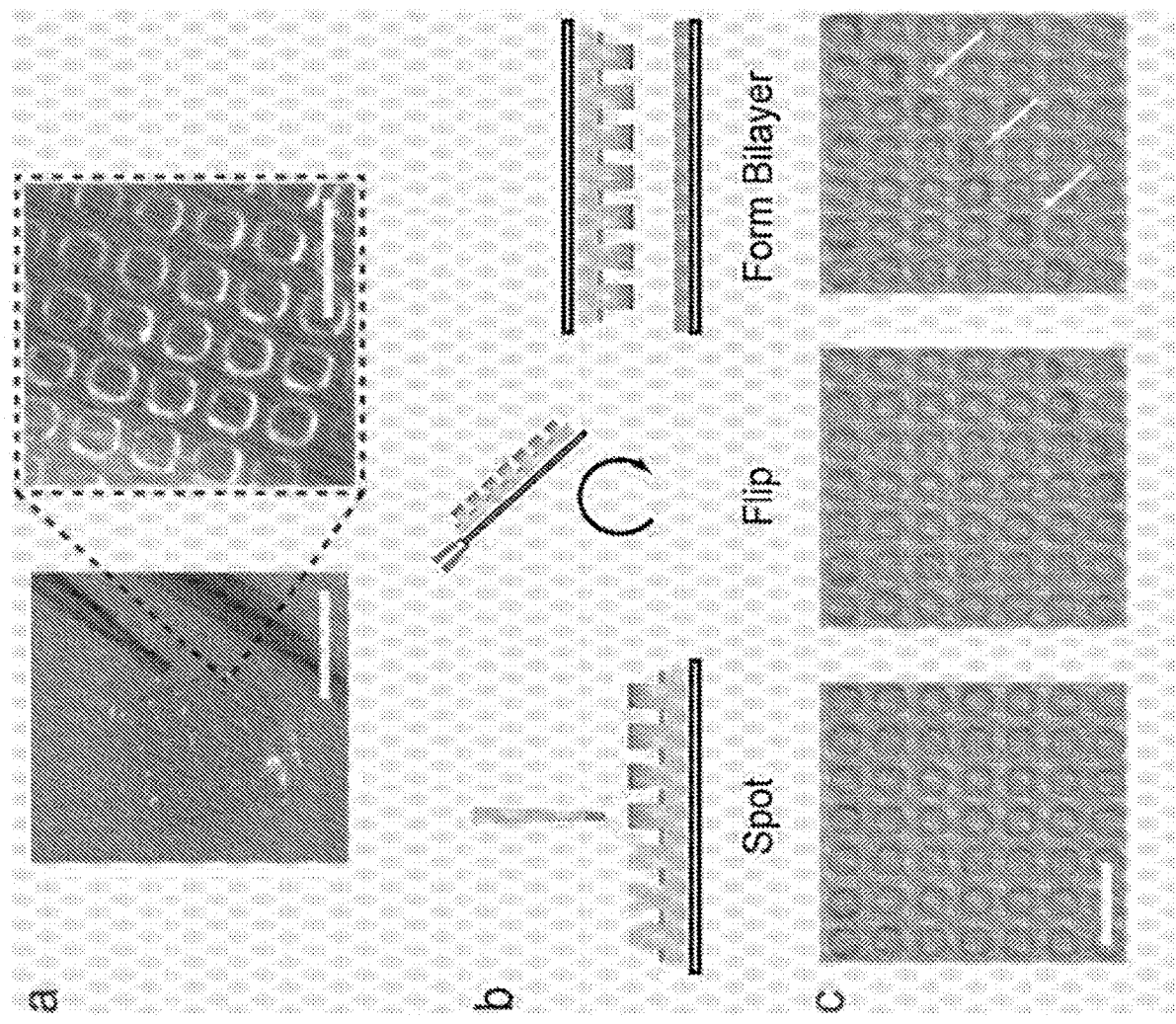
Figure 3:
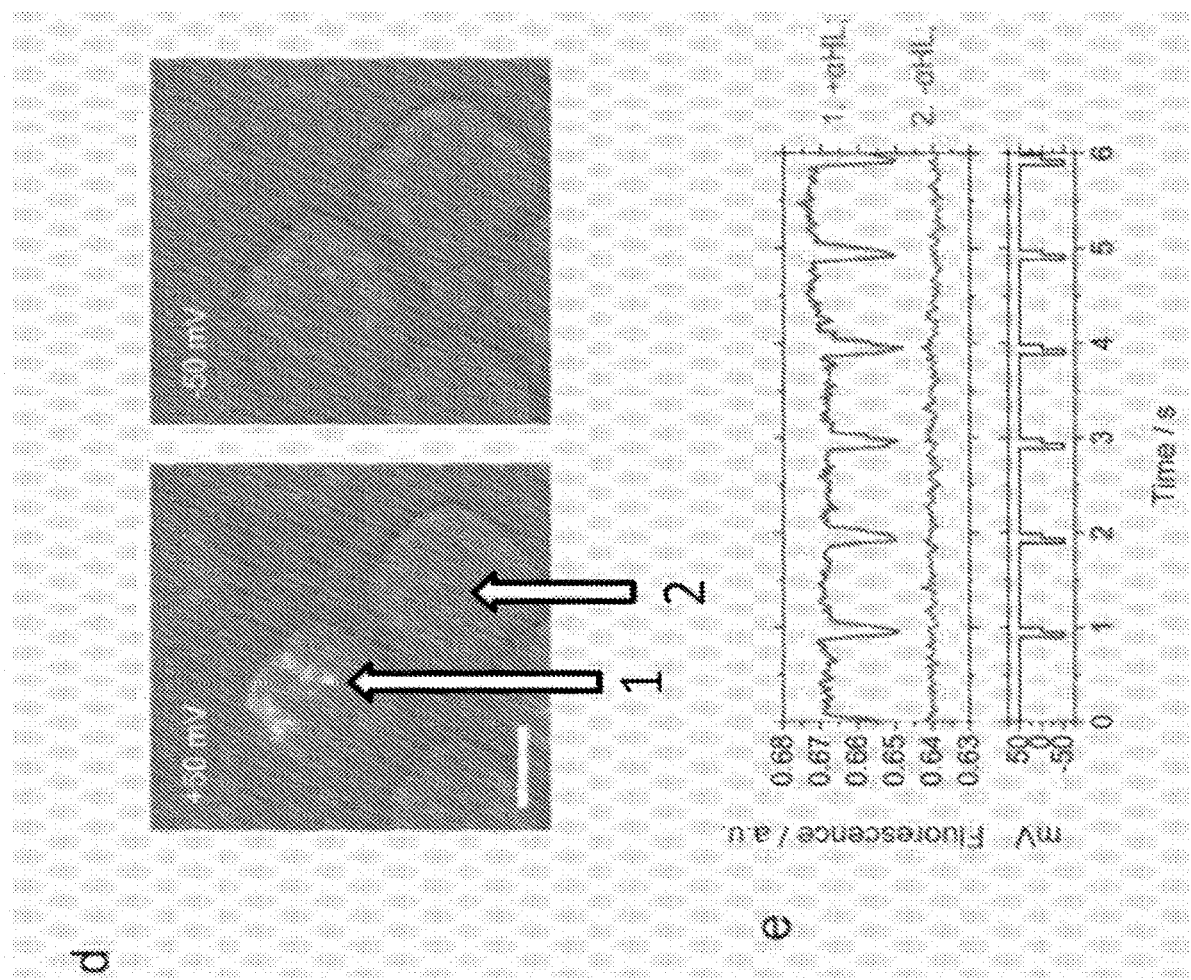
Figure 20:
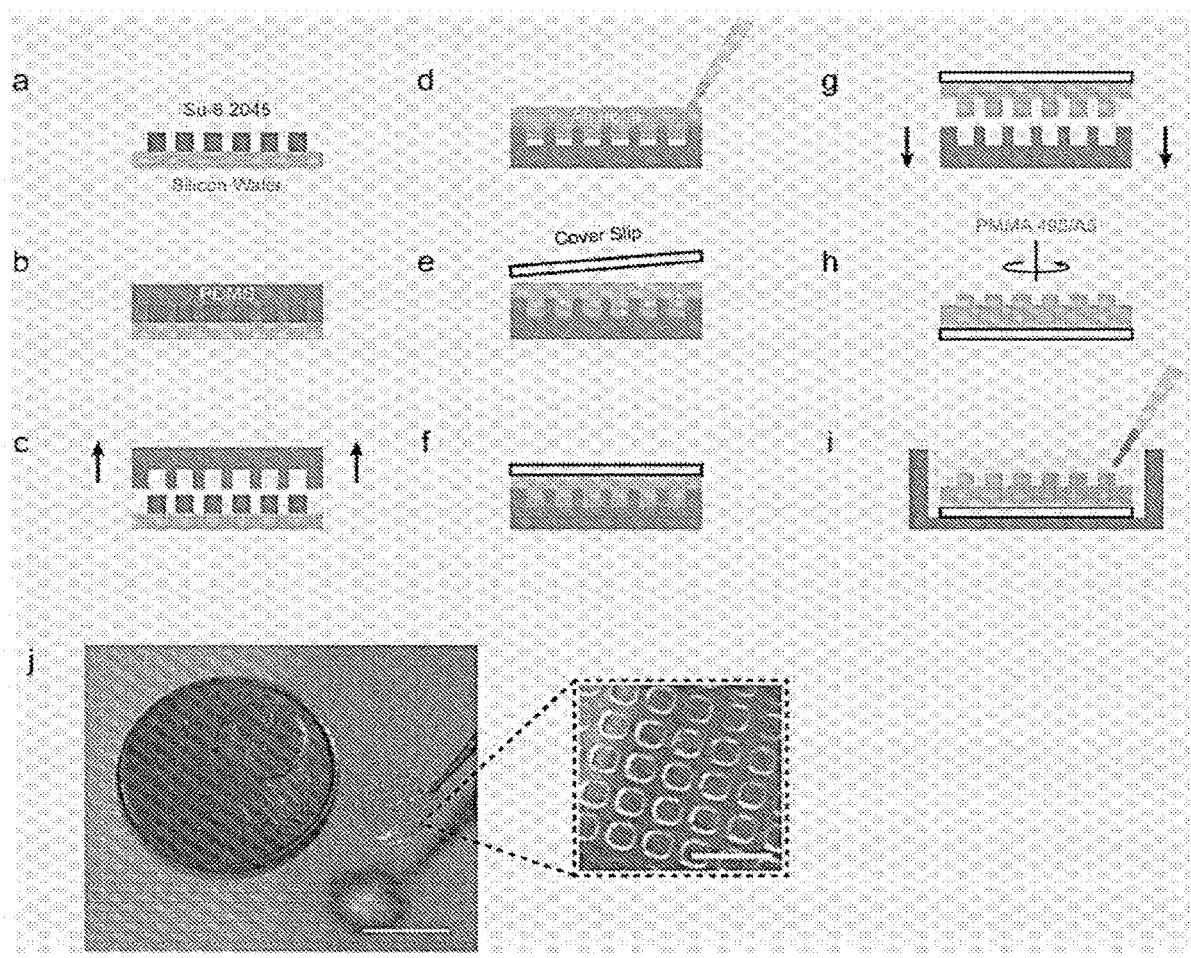

FIG. 3|Optical single channel recording in a multiplexed HHBa chip. a, A casted hydrogel chip, scale bar: 4 mm (FIG. 20). The image inset shows an array of micro-pillar patterns on the chip surface, scale bar: 140 µm. b, The diagram of a complete HHBa measurement procedure. Biological samples (αHL) are spotted onto the pillars (FIG. 22) and then the chip is flipped over to form HHBa with the substrate agarose in lipid/oil (FIG. 21). c, Bilayer array detachment. To show the edge of the bilayers, after HHBa formation, the chip is lifted gradually to detach the bilayers. Clear boundary lines between formed and un-formed bilayers can be visualized (white arrows). Scale bar: 140 µm. d, The intensity change of the fluorescent spots in the HHBa with +/− applied potential. αHL is spotted onto specific pillars (arrow 1). The inserted pores show strong/weak fluorescence spots at +/−50 mV. Each spot represents a single inserted nanopore. Scale bar: 35 µm. The fluorescent image is background normalized for optimized image contrast (FIG. 23). e, The fluorescent trace of the areas in d (pointed by arrows 1 and 2) with voltage protocols. A nanopore shows on/off fluorescent levels with +/−50 mV applied potential. The un-spotted HHB (purple arrow) shows no pore insertions and the fluorescence stays constant with voltage protocols.

Figure 4:
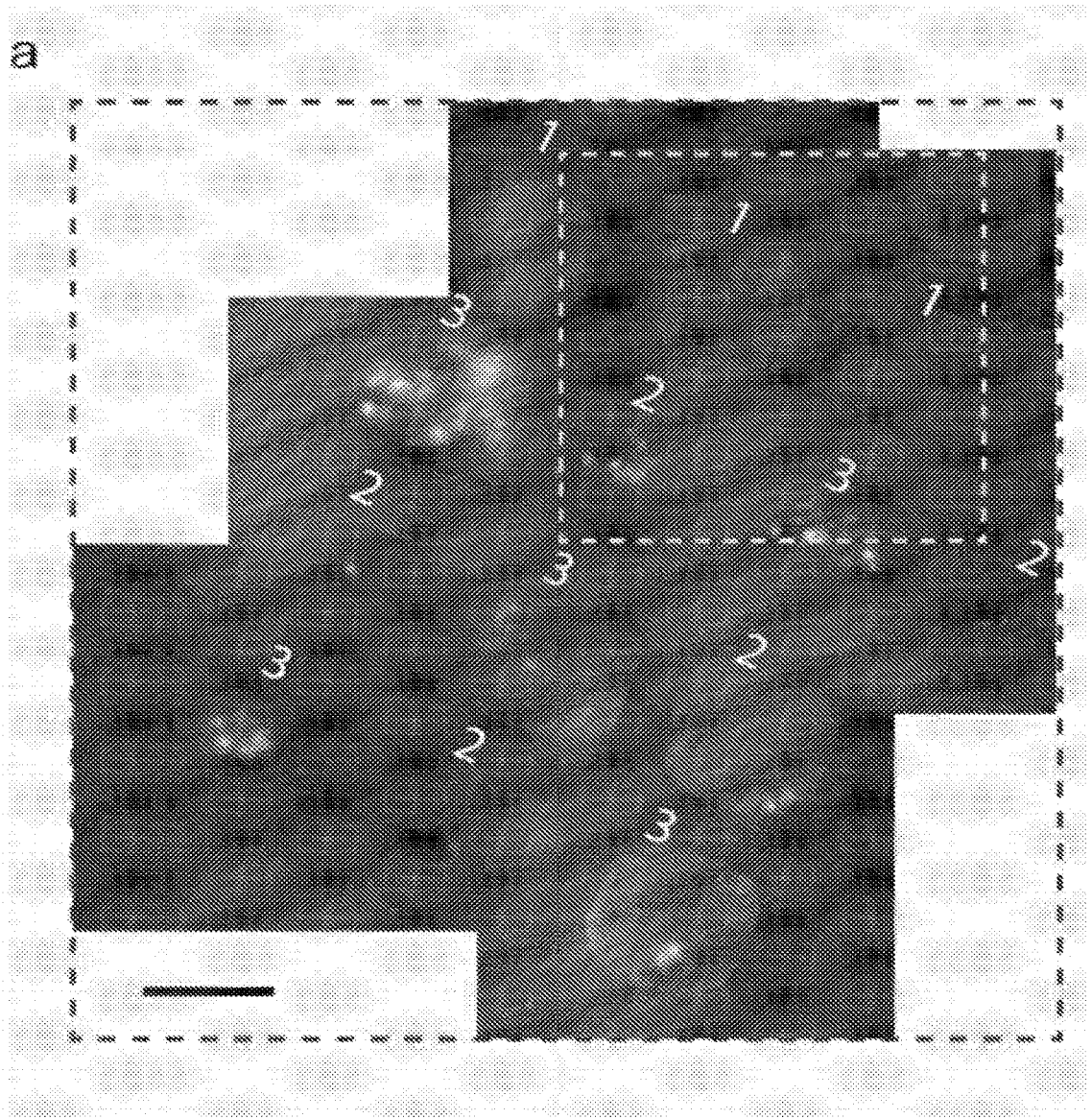
Figure 4:
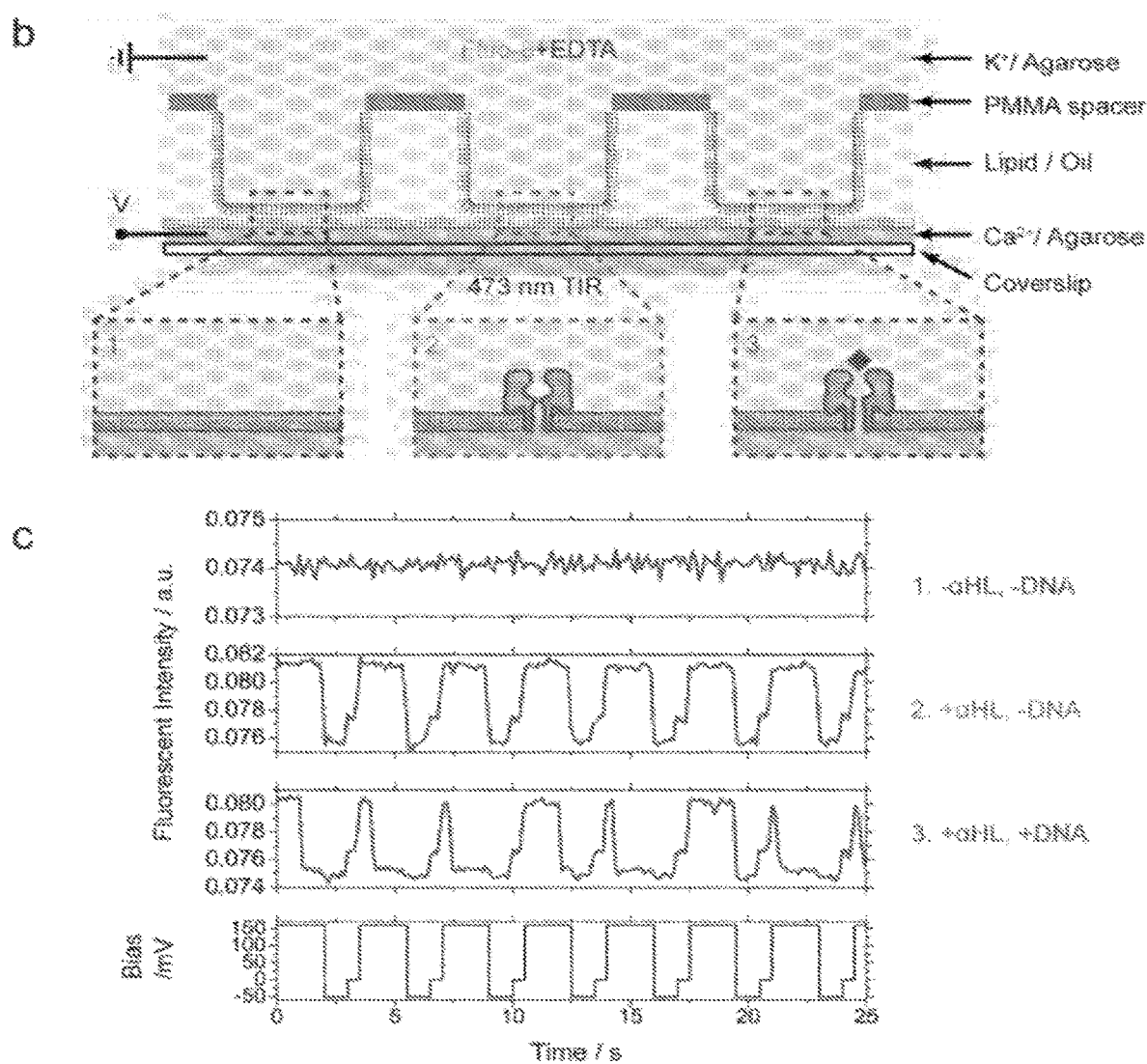

FIG. 4|Parallel biological sensing in HHBa. a, Stitching multiple fluorescence images (FIG. 24) to show a larger area of the chip with multiple types of biological samples (1. −αHL, −DNA; 2. +αHL, −DNA; 3. +αHL, +DNA). A single frame (the yellow/white dotted square) accommodates 4 bilayers at a time. Scale bar: 40 µm. b, The diagram of the HHBa measurement in TIRF mode. By analyzing the fluorescent intensity of each spot, each HHB could perform an independent nanopore measurement in single molecule. c, Analyzing single molecule nanopore activities in parallel. The fluorescent traces are simultaneously recorded from nanopores in different bilayers of the array (a, yellow/white square). The unspotted HHB shows constant fluorescence (Trace 1). However, the HHB loaded with αHL shows synchronized fluorescence change with voltage protocols (Trace 2). DNA ($C_{40}$) blockage events are only detected in Trace 3.

FIG. 5|The DHB measurement device. The device is manufactured as reported before[8] with a CNC milling machine (Modela MDX-40, Roland). a-c, The standard three-view drawing of the DHB device used in the experiment. Scale unit: mm. The agarose (0.75% low melt agarose) coated coverslip sticks to the bottom of the plastic plate when molten agarose (2.5% low melt agarose) is filled into the device (b). d, The actual DHB measurement chamber as demonstrated in (a-c). Inlet (arrow A)/Outlet (arrow B) holes on the device is designed to facilitate the filling of molten agarose. The extra hole on the outlet side helps air bubbles to escape during the filling. Each one of the 16 holes (central part of the device) accommodates a single DHB. However, only one DHB can be monitored simultaneously.

Figure 6:
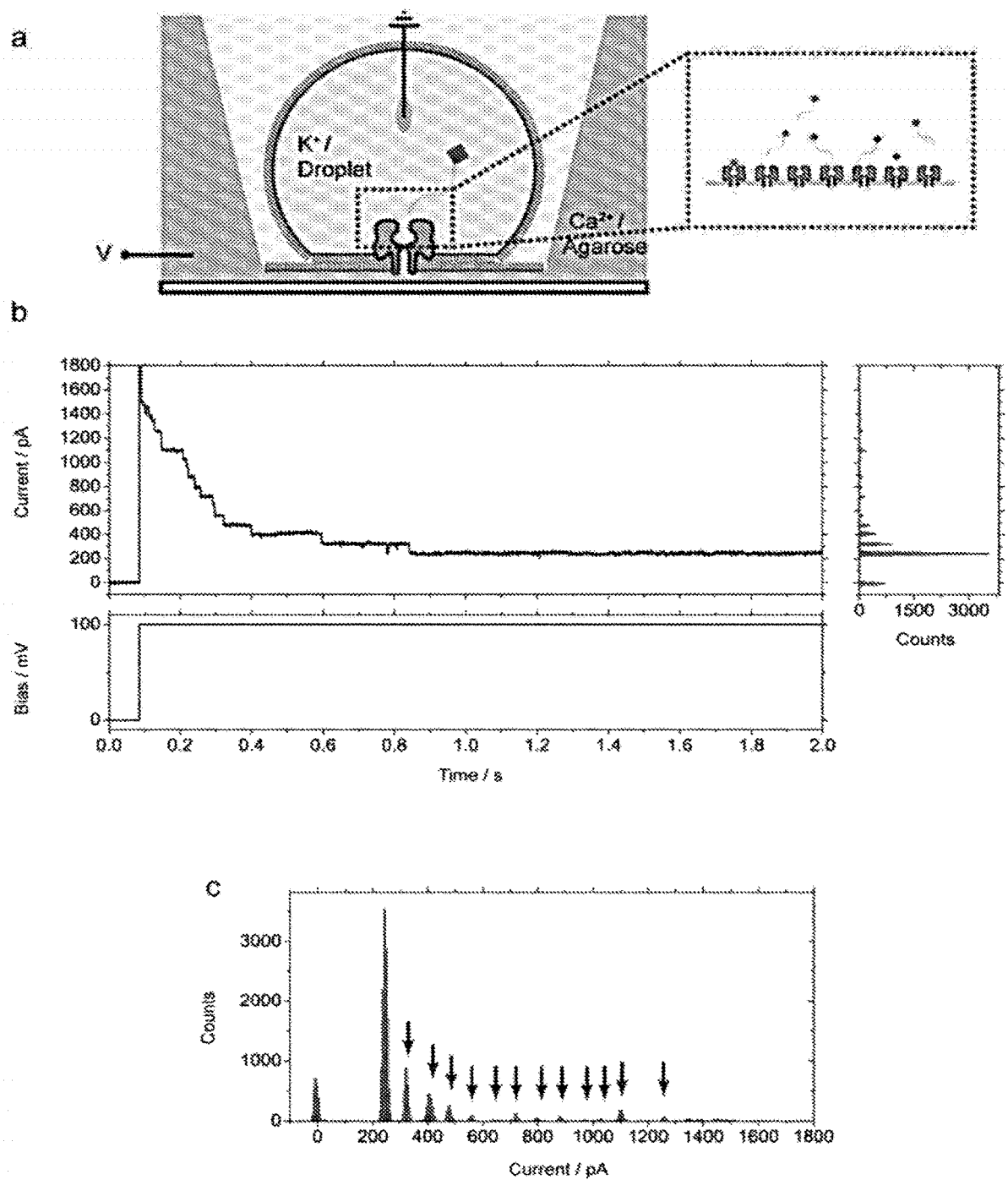

FIG. 6|The electrical measurement in the DHB. a, The schematic diagram of the electrical measurement in a DHB. Nanopores and streptavidin tethered ssDNA (C40, 267 nM) are placed in the droplet. There are multiple nanopores inserted in the DHB and the total ionic current is recorded by the patch clamp amplifier. b, A representative electrical trace of DNA blockages in DHB. At +100 mV, the current transiently achieves ~1500 pA. Then, streptavidin tethered ssDNA in the droplet starts blocking each pore sequentially, which appears as a step shaped trace in the current. c, The histogram of the electrical trace in (b), The separations between the adjacent peaks (82.9±6.5 pA, N=12) is comparable to the typical DNA blockage amplitude in a PLM measurement.

Figure 7:
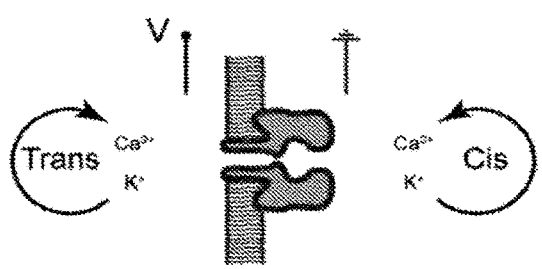
Figure 7:
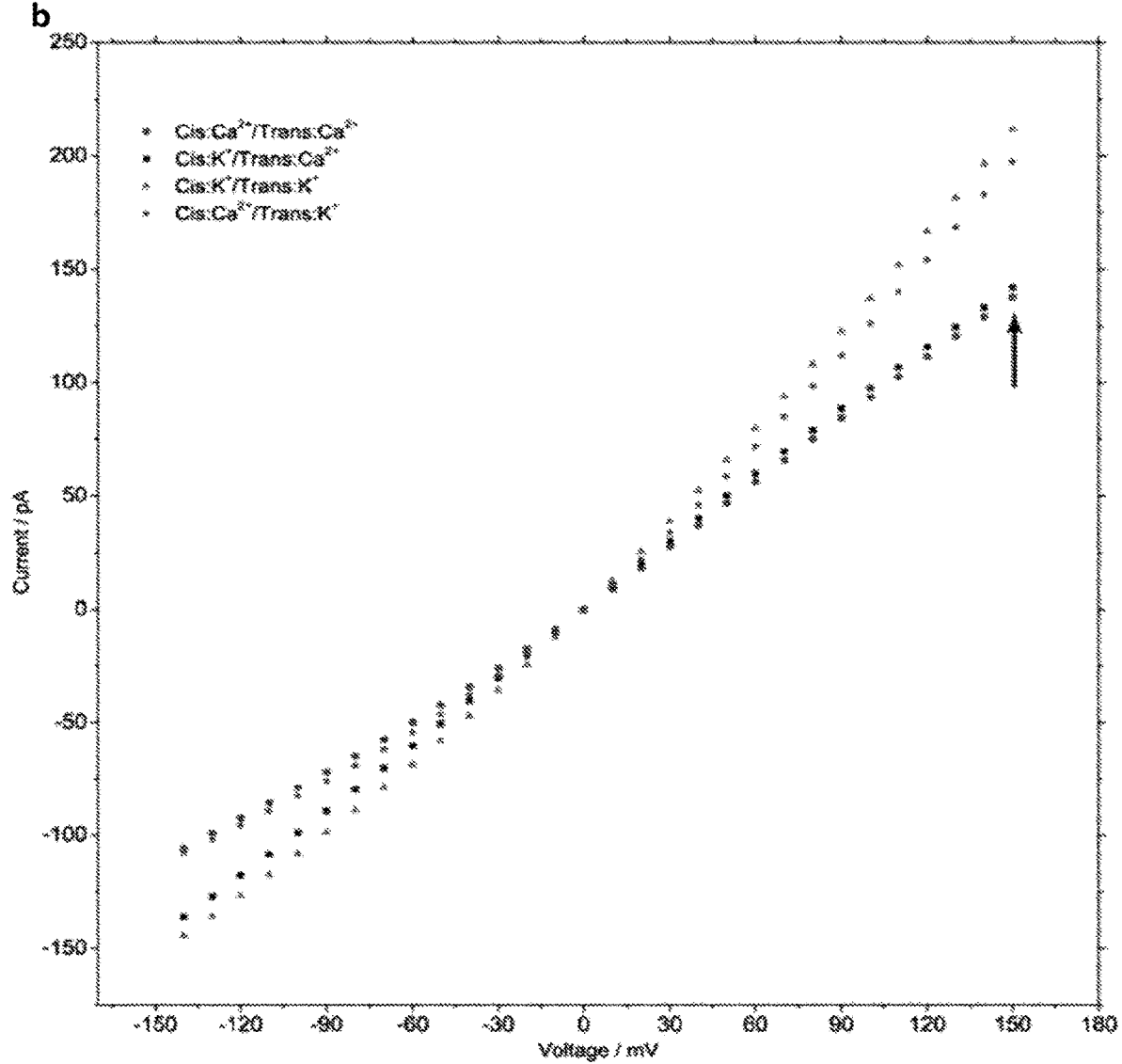

FIG. 7|Current-Voltage (IV) curve. The IV curve of a single nanopore is measured in the PLM. IV measurements for all four buffer combinations in Cis and Trans chambers are recorded. a, The schematic diagram of IV curve measurement with PLM. The Cis side is defined as the chamber with nanopores and is electrically grounded. To compare the conductance change of the same nanopore with different buffer combinations, the buffer in either the Cis or the Trans side are exchanged without breaking the bilayer. b, The IV curve measurement with all four different combinations of calcium chloride (0.66 M CaCl2, 8.8 mM HEPES, Ph 7.0) and potassium chloride (1.32 M KCl, 8.8 mM HEPES, Ph 7.0) buffer. Please note that at positive potential the conductance of a single pore is lower (as pointed out by the arrow) when the calcium chloride buffer is placed on the Trans side.

Figure 8:
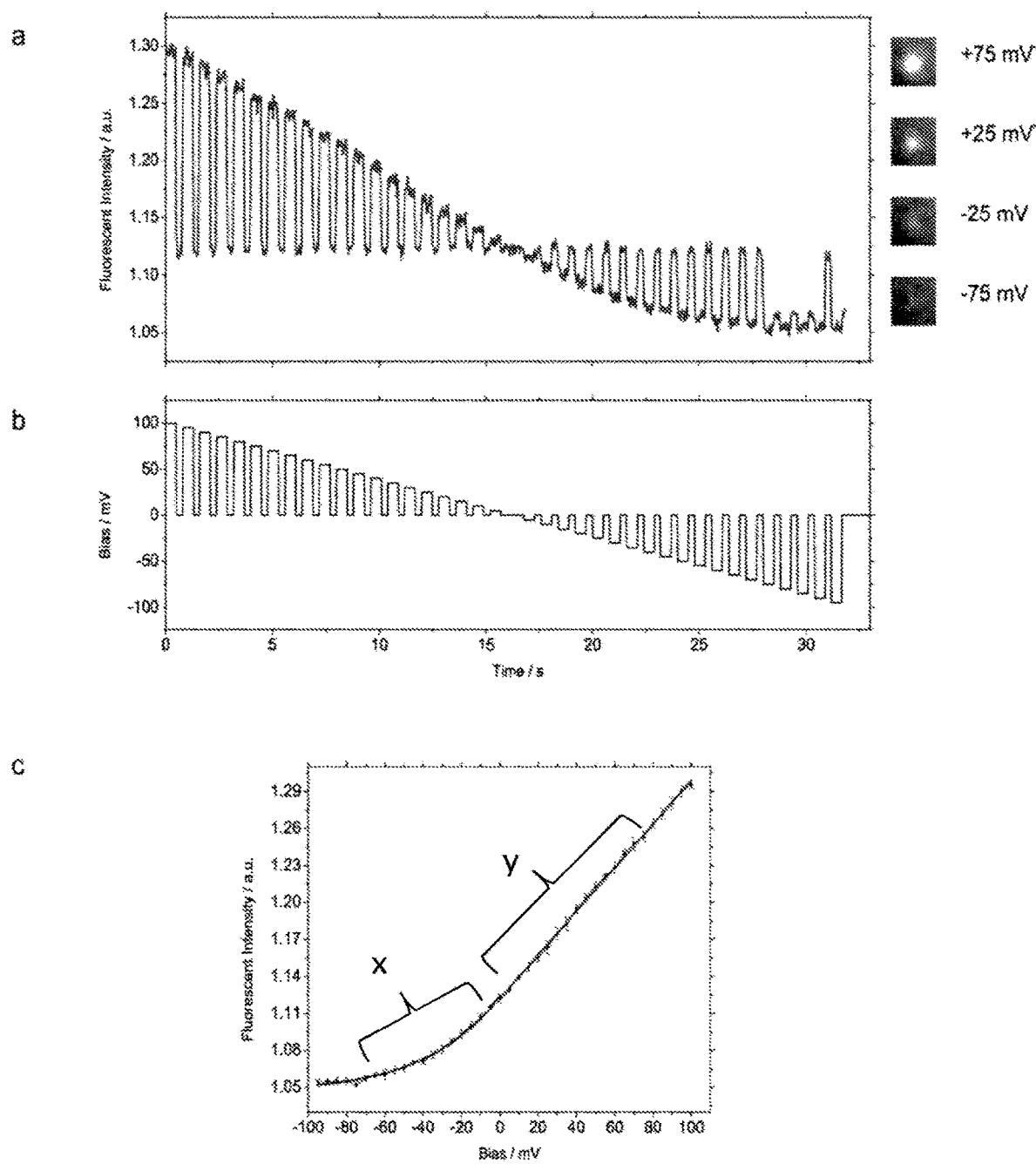

FIG. 8|Fluorescence-Voltage (FV) curve. In OPC, the fluorescent intensity, which is proportional to the $Ca^{2+}$ flow rate, is modulated by the applied potential. a, The fluorescence of a single nanopore at different applied potentials. The fluorescent intensity gradually drops with the potential ramp from +100 mV to −100 mV. Selected image frames on the right demonstrate the change of the spot brightness at different potentials. b, The applied voltage protocols. c, The FV curve of an open nanopore. Linear curve fitting (y) is performed for the FV curve at positive potentials and exponential curve fitting (x) is performed at negative potentials.

Figure 9:
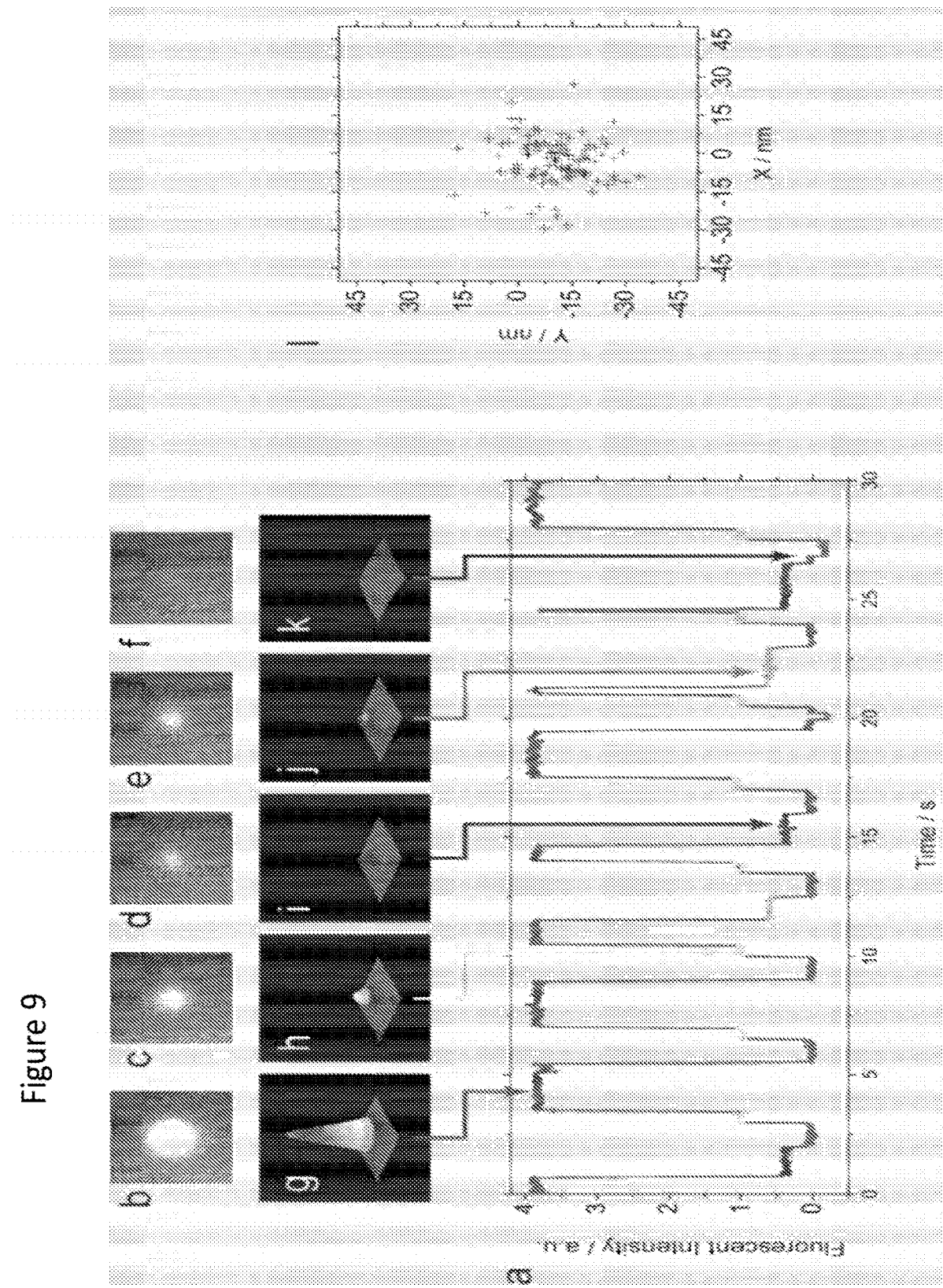

FIG. 9|2D Gaussian fitting and position tracking. The demonstrated data is based on the OPC of a single nanopore in DHB. a, The fluorescent trace containing 2 types of DNA blockage events. b-f, Raw image frames of a single fluorescent spot aligned with the trace. g-k, The 2D Gaussian fitting result of the raw images in (b-f). The colour coding of the cone, which is consistent with the fluorescent intensity, helps to resolve subtle differences in the residual fluorescence of C40 (i) and X5 (j) blockage events. The position tracking based on 2D Gaussian fitting. The position of the pore is defined as the centre of the fitted cone. Here the tracking result from 100 frames is demonstrated. l, The standard deviation on the x direction is 11.33 nm and on the y direction is 13.83 nm.

Figure 10:
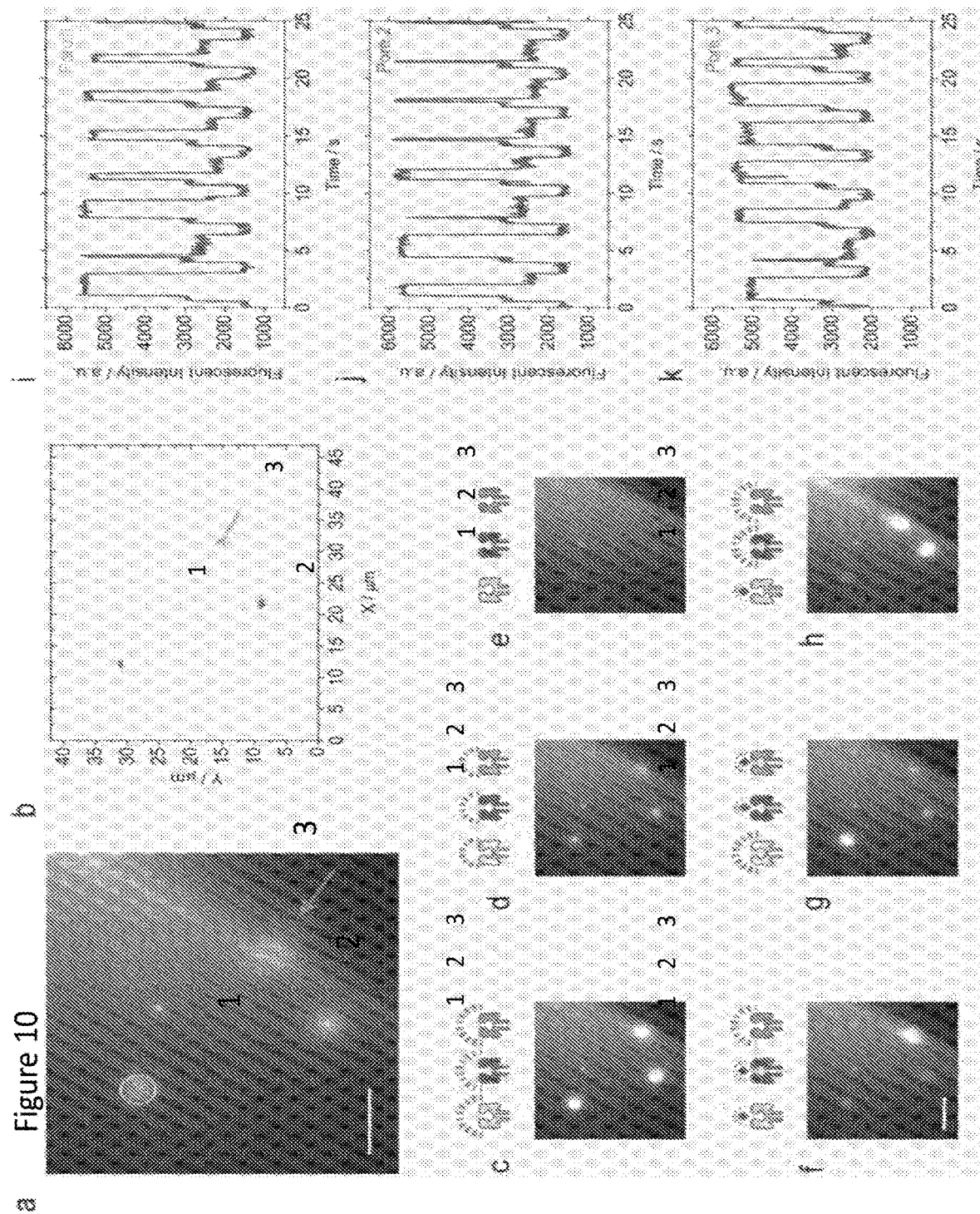

FIG. 10|The demonstration of parallel recording. Multiple nanopores can be tracked and recorded simultaneously. a, The superimposed image from 1000 frames containing 3 nanopores. The position trackings are marked with colour circles (pore 1: yellow; pore 2: pink; pore 3: cyan). Pore 3 (cyan), which is forced to drift by the edge of the bilayer, generates a blurry tail from the tracking (arrow) in the superimposed image. Scale bar: 10 μm. b, The tracking result of the 3 pores. The track of pore 3 shows a stretched line due to the pore drifting. c-h, Selected image frames of pore activities from the 3 pores. Cartoon schematics on top of each frame demonstrate the independent pore activities from the 3 pores. Streptavidine tethered C40 is placed in the droplet to block the pore. Scale bar: 10 μm. i-k, Independent fluorescent traces from the 3 pores in the same field of view.

Figure 11:
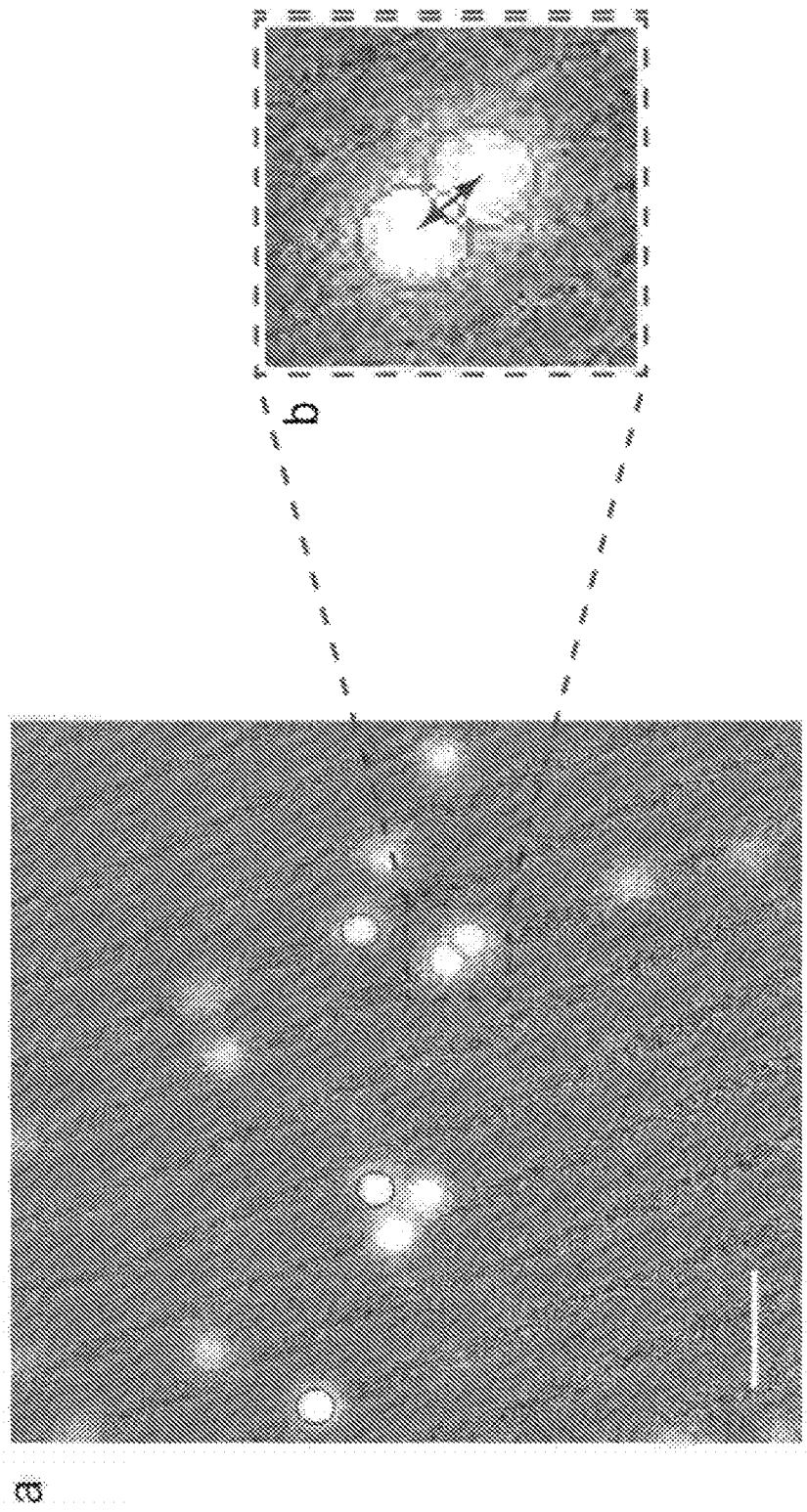

FIG. 11|The minimum spatial resolution with optical single channel recording. In principle, fluorescent spots which are separated with more than their half height width should be resolved. To test the minimum spatial resolution with the bilayer, the agarose coating below the DHB is over hydrated to increase the mobility of the bilayer. Pores drift stochastically within the DHB and generates various pore to pore distance with time. The tracking resolution is thus estimated by analyzing pore pairs with tiny separations. a, The image frame containing many nanopores. The tracking is marked by colour coded circles on the spots. Scale bar: 15 μm. b, This image demonstrates the minimum pore to pore distance that the tracking algorithm can still distinguish. The pore to pore separation is 3.2 μm.

Figure 12:
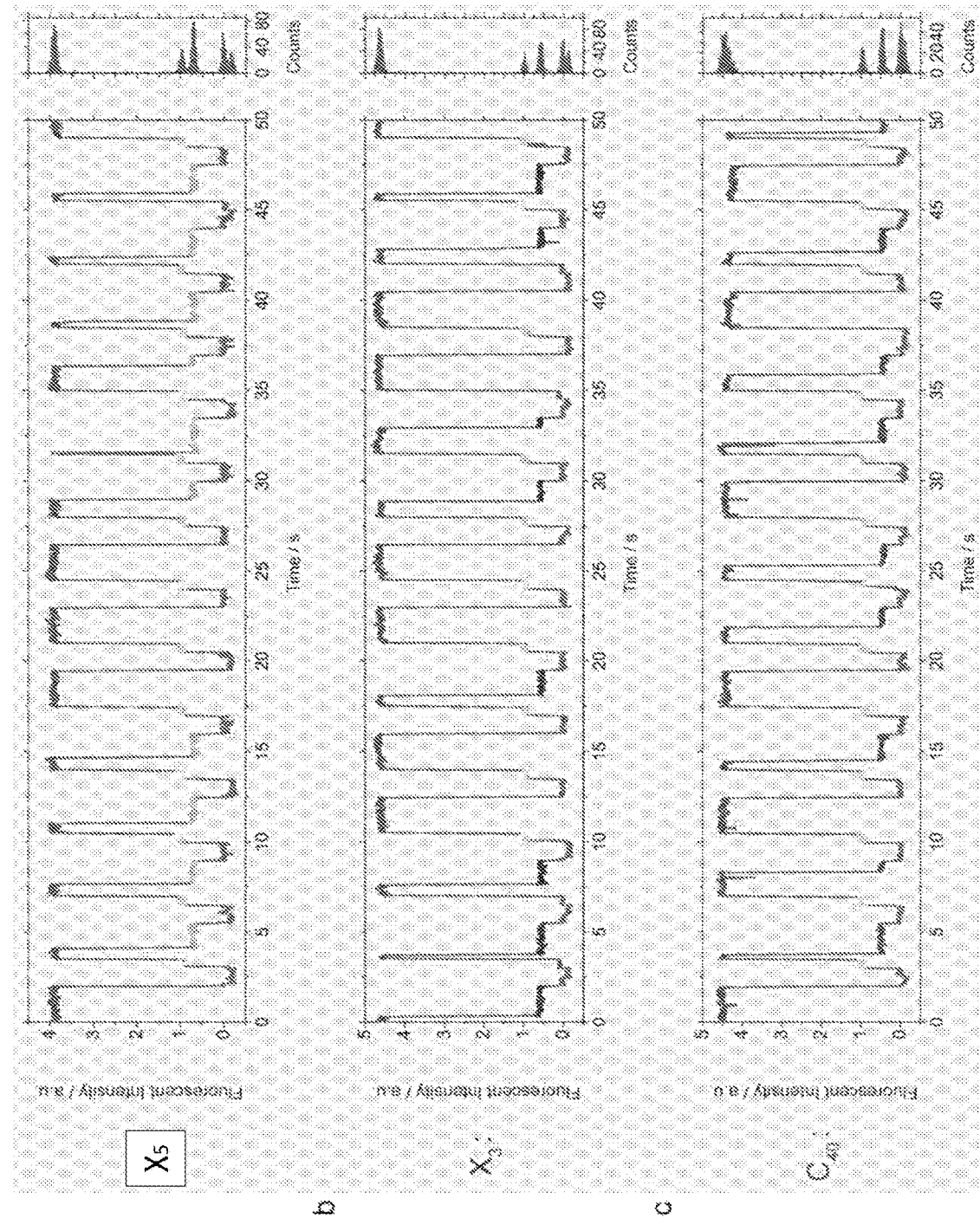

FIG. 12|DNA blockages in the fluorescent traces. Three fluorescent traces are demonstrated to show different types of DNA blockages in DHB. a, The representative fluorescent trace of X5 DNA blockages. b, The representative fluorescent trace of X3 DNA blockages. c, The representative fluorescent trace of C40 DNA blockages.

Figure 13:
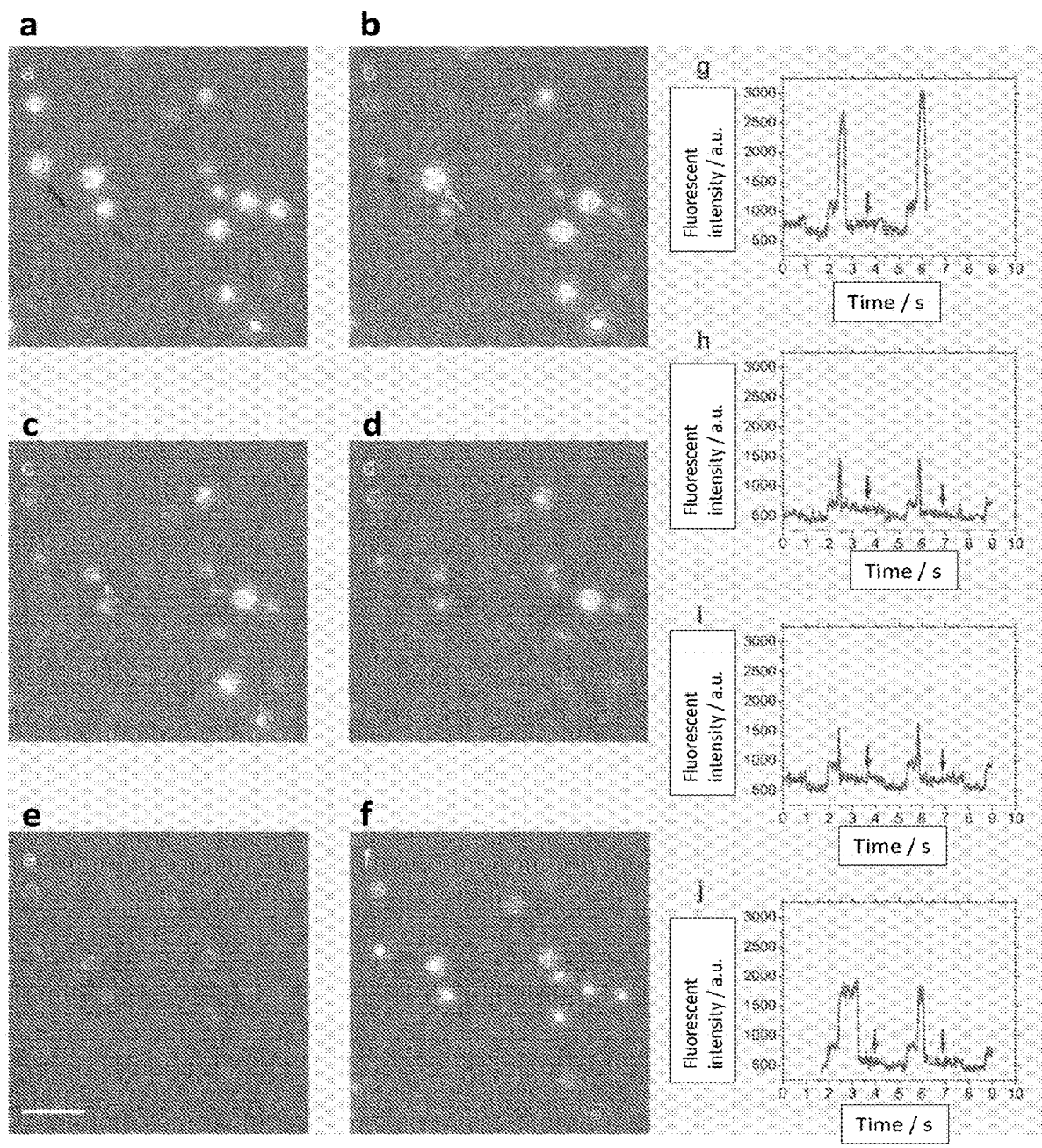

FIG. 13|Simultaneous recordings of 12 pores. The images are recorded in DHB. a-d, Selected image frames containing the colour coded tracking markers over 12 fluorescent spots. Solid arrows point to open pores that are blocked (as pointed by the dashed colour arrows) in the next frame. Potential: +100 mV. Scale bar: 15 μm. e, The image frame at −50 mV. f, The image frame at 0 mV. g-j, 4 selected fluorescent traces with DNA (C40) blockage events (blue arrows).

Figure 14:
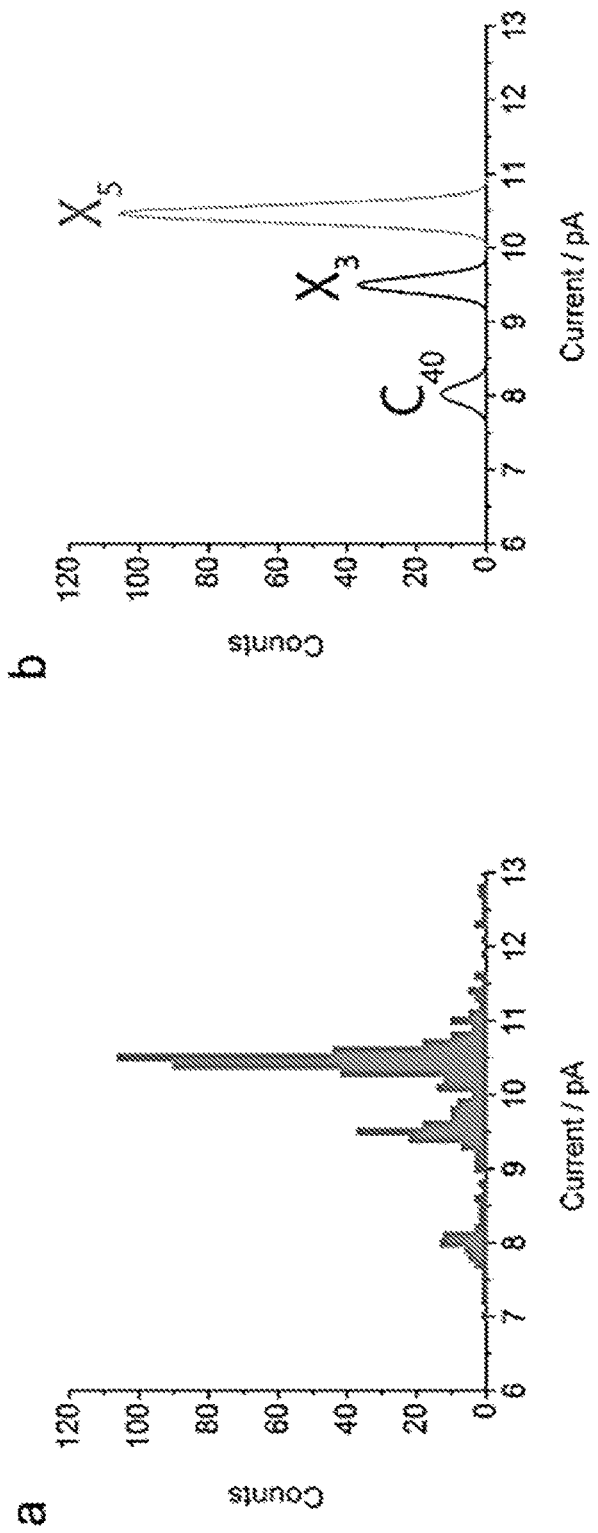

FIG. 14|The histogram of the residual current. The experiment is performed with a single nanopore in PLM. Three types of DNA (streptavidine tethered C40, X3 and X5) are mixed with the same concentration (89 nM each). ssDNA with abasic nucleotides replacements in sequence may have an advantage in captured rate due to the reduced molecular weight and the increased mobility. a, The histogram based on 1000 DNA blockage cycles. b, the corresponding Gaussian fitting result.

Figure 15:
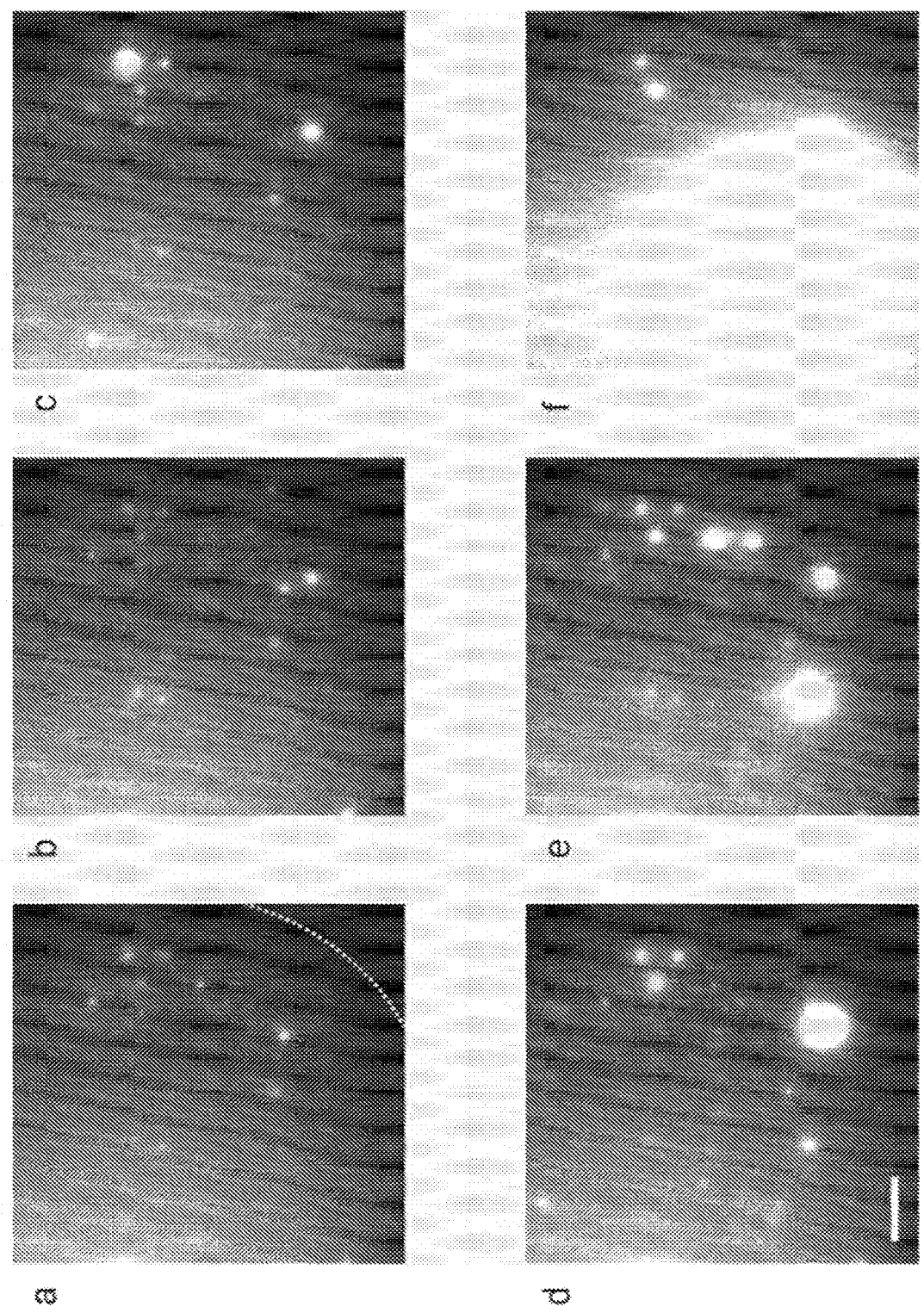

FIG. 15|Electroporations at high potentials. Electroporations, which are non-specific holes in the lipid membrane, generate huge ion leakage and may rupture the bilayer. In a single large DHB (>1 mm2), high applied potential (>160 mV) normally leads to electroporation formation. The bilayer stability against high potentials is reduced by increasing size of a single bilayer. a-e, Electroporation formation process at high potentials. Electroporations are recognized as bright spots with abnormal sizes and vigorous intensity fluctuations. On the contrary, a properly inserted αHL shows consistent and stable fluorescent levels. The yellow/white dashed line represents the boundary of the DHB. Scale bar: 20 μm. f, The DHB is irreversibly ruptured by high potentials, which generates extremely strong fluorescence due to abundant $Ca^{2+}$ and Fluo-8 binding.

Figure 16:
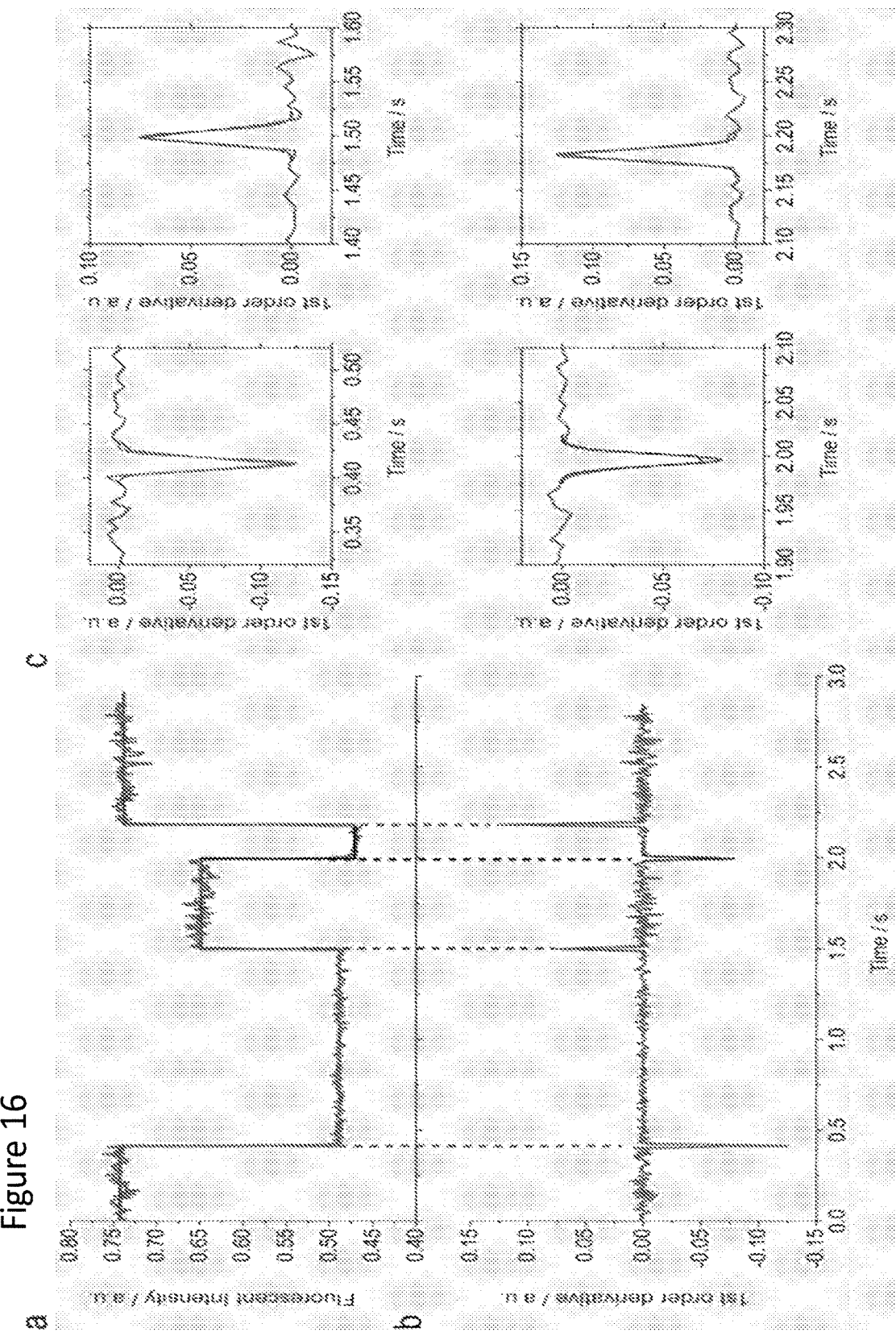
Figure 16:
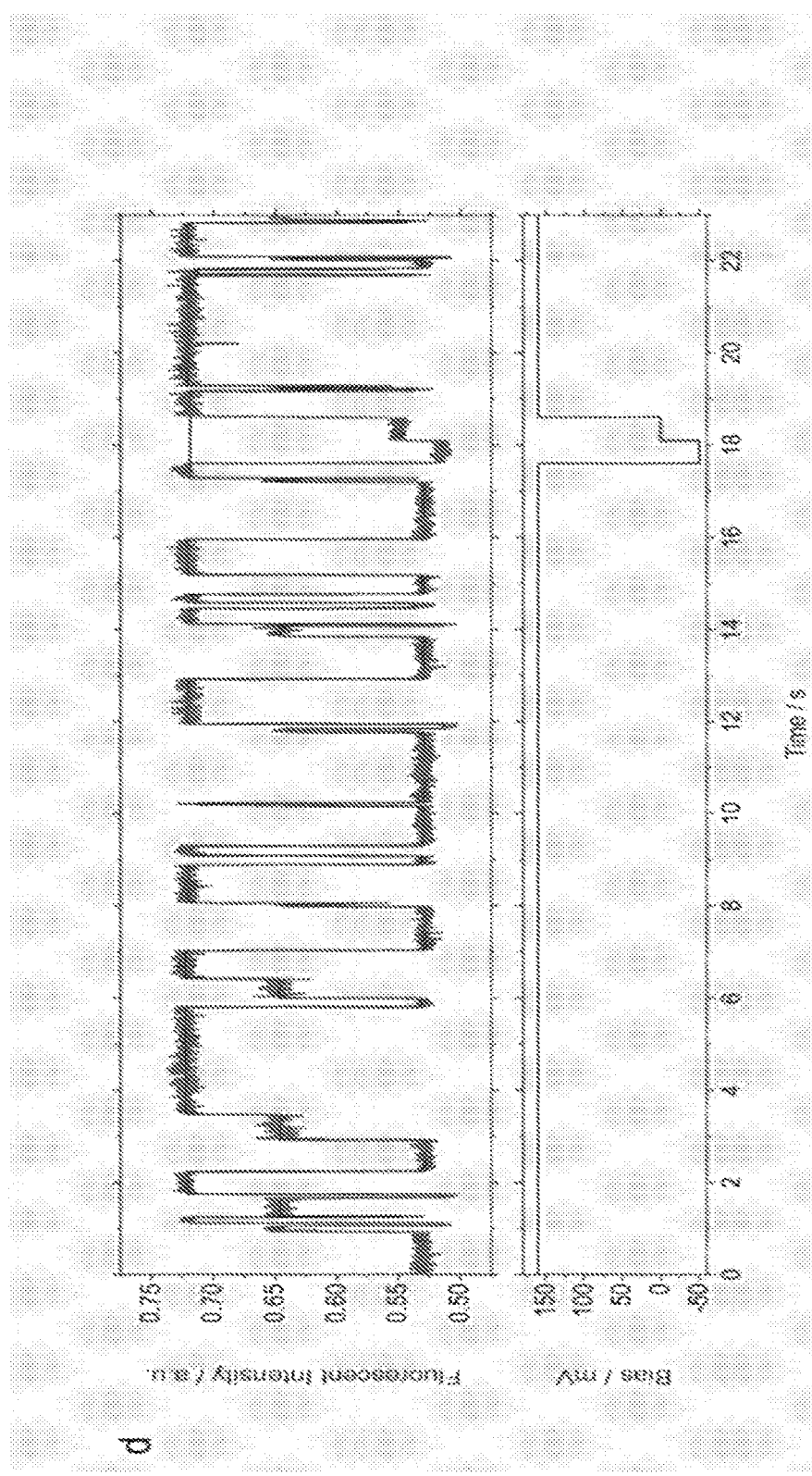

FIG. 16|The fitting algorithm for miRNA unzipping traces. The fluorescent trace is recorded in DHB with +160 mV potential. Although the minimum exposure time for a single frame in OPC is 3 ms for now. A fitting algorithm is developed to break this time resolution even further. In general, sharp transitions in the fluorescent trace appear as peaks in the 1st order derivative result. By 2D Gaussian fitting of these peaks, the accurate transition time between states could be estimated from the fitted centre. a, A representative miRNA unzipping cycle. b, The 1st order derivative of the trace in a. The fitted peaks determine the accurate transition time (dash lines) between molecular states. c, The peaks in the 1st order derivative trace and the fitting. d, Automated event selection. A typical miRNA unzipping event has 3 characteristic state levels (FIG. 2a). By analyzing the amplitude and the transition time of the fluorescent trace, miRNA unzipping events can be picked up automatically with a homemade labview program. Periodically, −50 mV is applied across the DHB to clear the pore from clogging. Partial events (0-1 seconds in d) and events at incorrect potentials (17.5-18.5 seconds in d) are not included for statistics.

Figure 17:
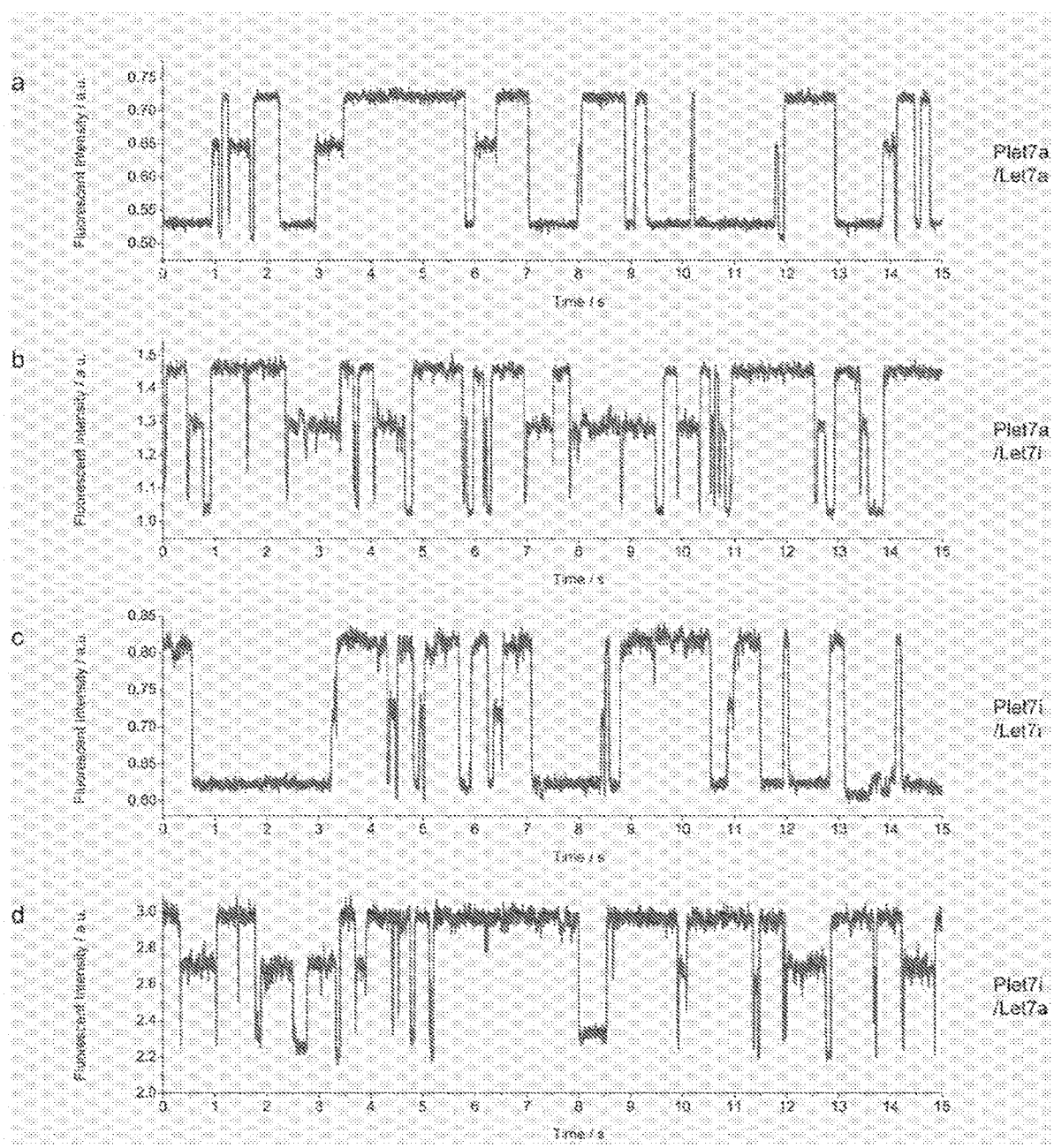

FIG. 17|miRNA unzipping in the 15 sec traces. The measurements are done in DHB. All four combinations of matched/mismatched probe/miRNA have been tested. In general, long T1 events (>1 sec) are only detectable when the miRNA is complementary to the probe. a, Plet7a/Let7a. b, Plet7a/Let7i. c, Plet7i/Let7i. d, Plet7i/Let7a.

Figure 18:
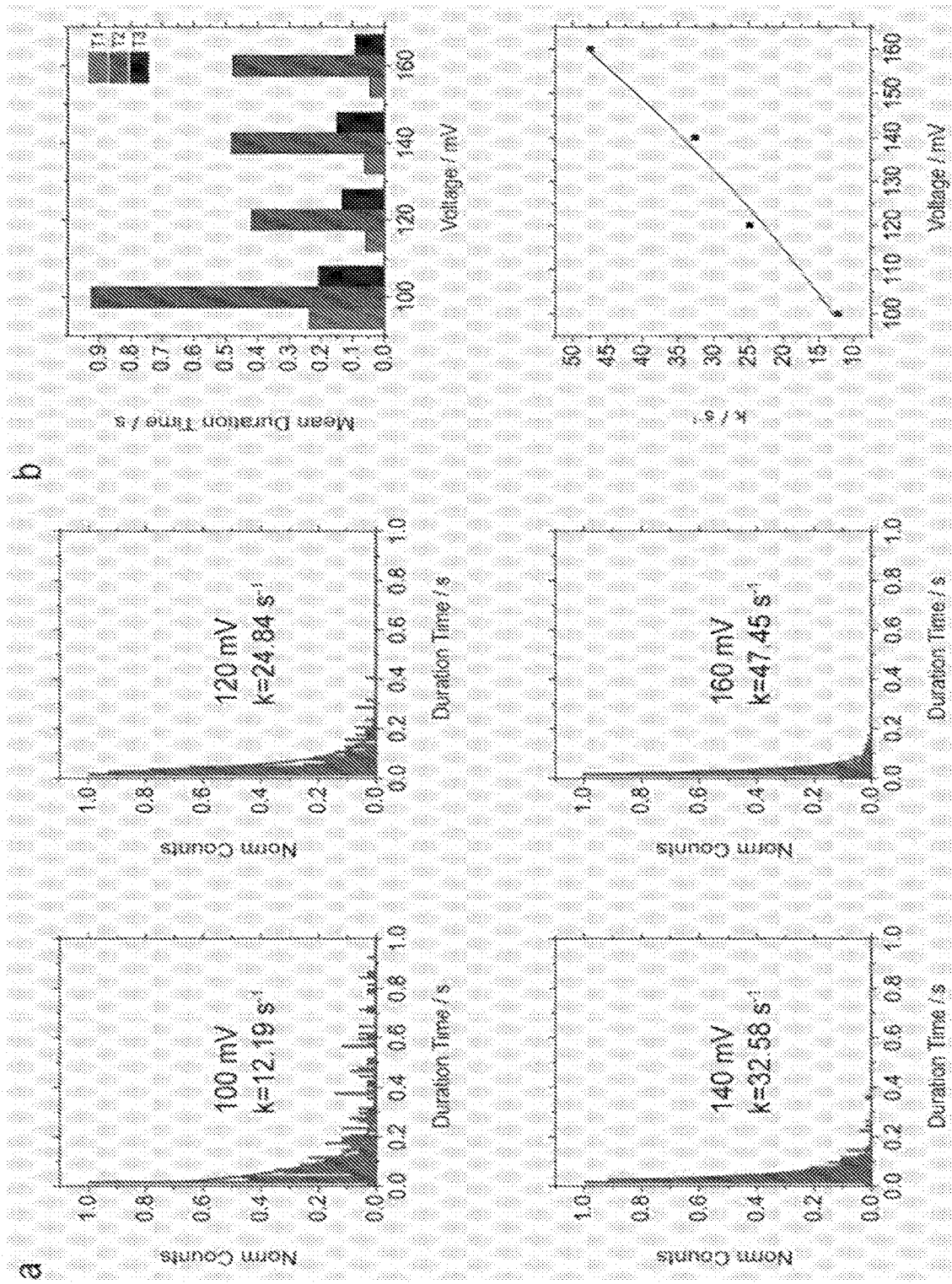

FIG. 18|Voltage dependence of miRNA unzipping for Plet7a/Let7i. At low applied potential (<120 mV), the duration time for T1 is normally too long (T1>10 s) for sequence complementary probe/miRNA combinations and the pore could be easily clogged by the hybridized sample without unzipping. Thus, a mismatched probe/miRNA sample (Plet7a/Let7i) is used to demonstrate the voltage dependence from 100 mV to 160 mV. a, The histogram of T1 at different applied potentials. The fitted rate constant in the distribution suggests that the unzipping is much faster at higher potentials. b (top), The mean duration time of T1, T2 and T3 at different potentials. The mean duration time of T1 is significantly longer at +100 mV. b (bottom), The plot of the rate constant vs. voltage with an exponential fitting.

Figure 19:
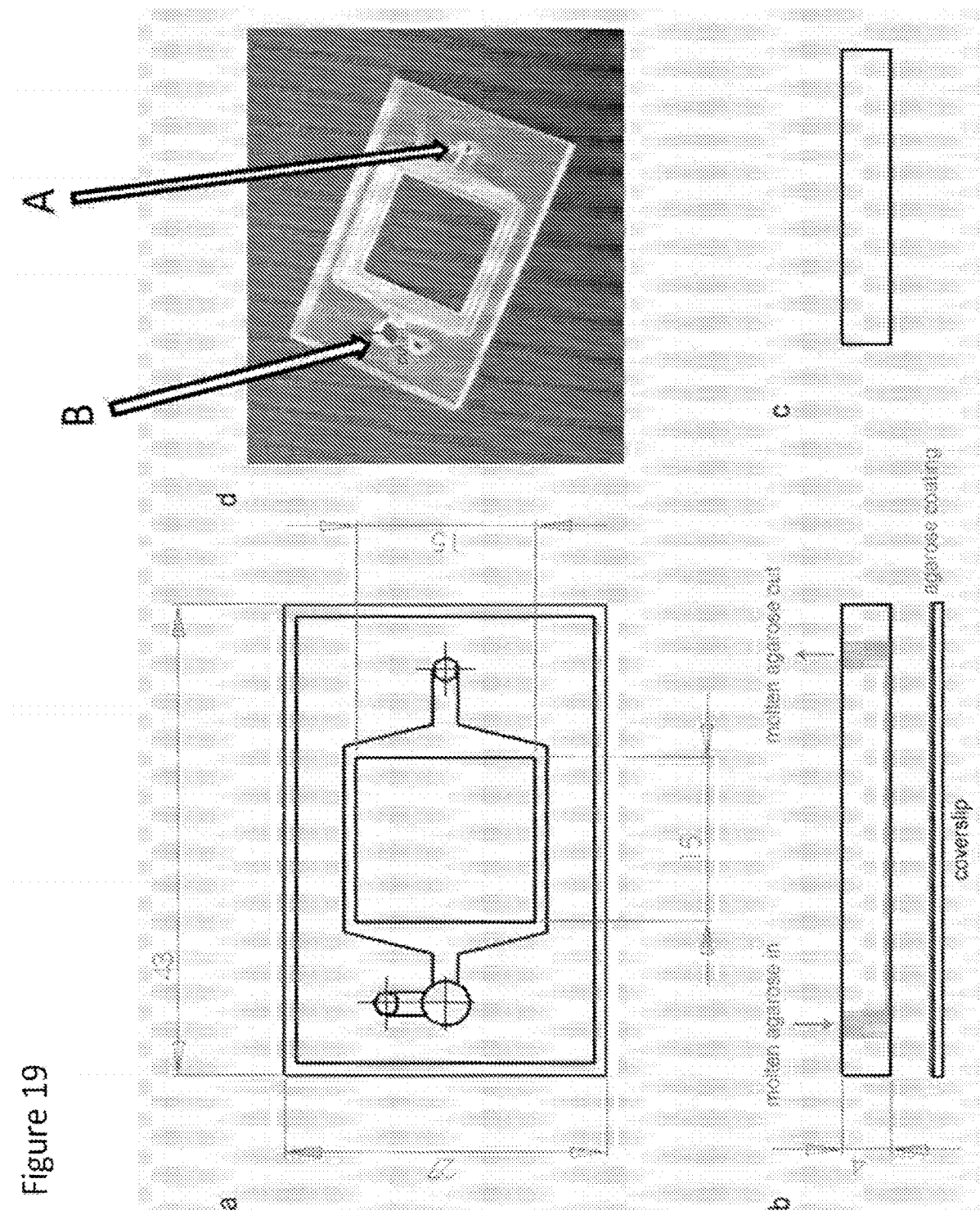

FIG. 19|The HHBa measurement chamber. The device is manufactured with a CNC milling machine (Modela MDX-40, Roland). a-c, The standard three-view drawing of the HHBa chamber used in the experiment. Scale unit: mm. The agarose coated (0.2% low melt agarose) coverslip sticks to the bottom of the device when molten agarose (2% low melt agarose) is filled into the setup (b). d, The actual HHBa measurement chamber. Inlet (arrow A)/Outlet (arrow B) holes on the device is designed for molten agarose to fill into the channel. The extra hole on the outlet side helps air bubbles to escape during the filling.

FIG. 20|The hydrogel chip fabrication procedures. The hydrogel chip is fabricated according to the following procedures. Step a-c is performed according to the standard soft lithography protocol3. Step d-f is similar to the fabrication of an agarose stamp9 and the PDMS mould can be reused for multiple times. a, Patterning of SU-8 pillars with the standard photolithography protocols (MicroChem). b, Casting PDMS wells with the SU-8 mould (a). c, Peeling off the PDMS from the SU-8 mould. d, Filling the micro-cavities of the PDMS mould with molten agarose (3% (v/v) agarose for routine use, 1.32 M KCL, 8.8 mM HEPES, 8.8 mM EDTA, Ph 7.0). e, Desiccator degassing. Air bubbles in the hydrogel chip needs to be removed and a piece of coverslip is immediately placed on the back of the hydrogel. f, Gelling of the agarose at low temperatures (4° C., 30 minutes). g, Peeling off the casted hydrogel chip from the PDMS mould. h, Spin coating (4000× rpm, 60 s) of PMMA 495/A5 (0.2% in anisole) above the hydrogel chip. Immediately after the spin coating, a PMMA film will form in the gaps between the pillars. i, Immersing the chip in hexadecane to avoid dehydration. Fluo-8 dye (1 µg/µL) is fused into the hydrogel and the. It takes ~4 hours to achieve a homogeneous distribution of the dye. The chip immersed in hexadecane can be stored at room temperature for >48 hours. j, Comparing the size of the chip with a 5 cent euro coin. Scale bar: 8 mm. The chip can be easily manipulated with a pair of tweezers. Image inset: Bright field microscopic image of the hydrogel pillars on the chip. Scale bar: 140 µm.

Figure 21:
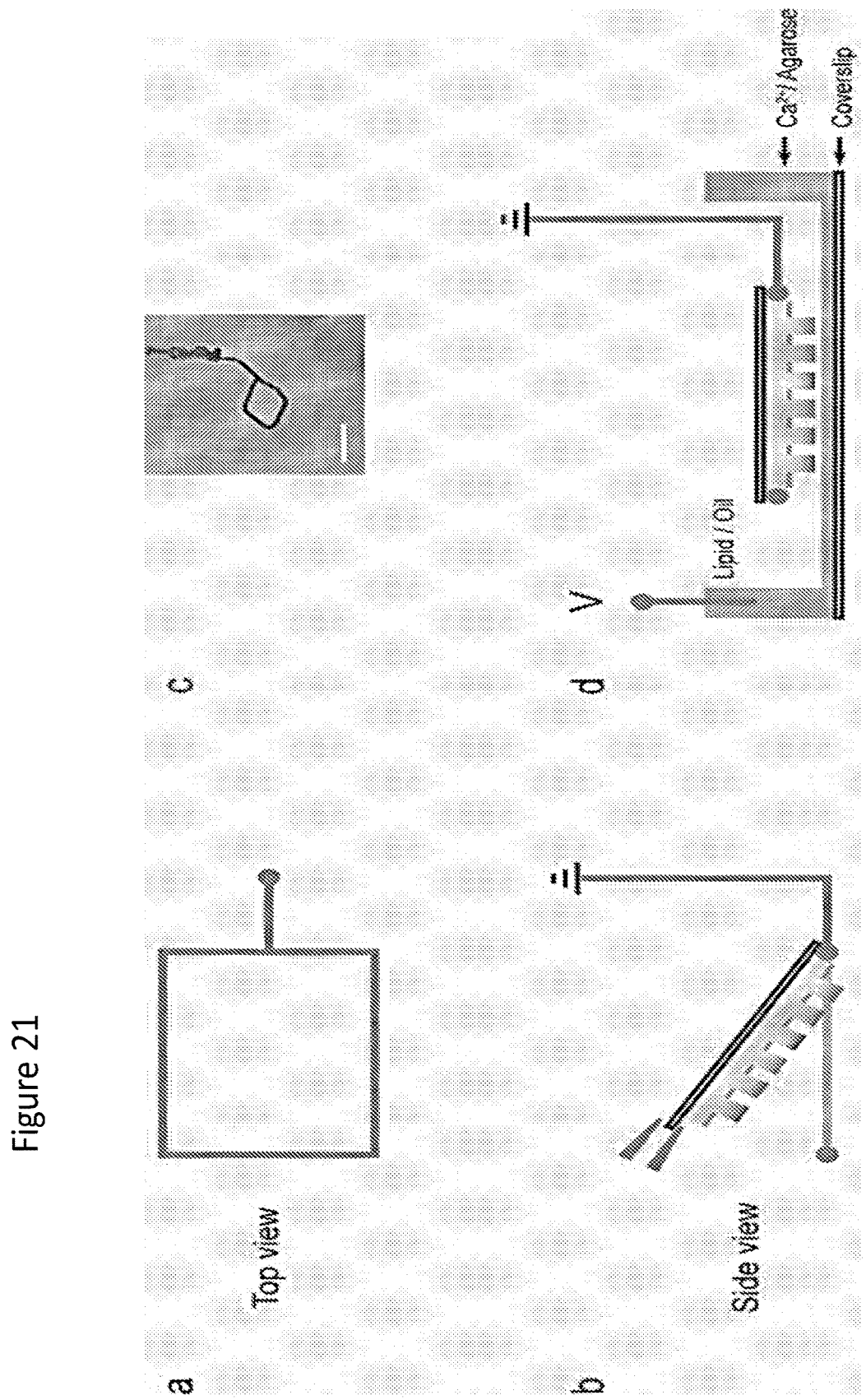

FIG. 21|The electrode for the HHBa chip. A special electrode ring (Ag/AgCl) is designed to hold the chip and secures the electrical connections. a, The top view diagram of the electrode. b, The side view diagram of the electrode with a chip. The chip is placed onto the electrode by a pair of tweezers. The electrode is coated with a layer of agarose to make the surface more hydrophilic so that the electrode and the chip spontaneously form a tight electrical connection upon physical contact. c, The actual electrode. Scale bar: 5 mm. d, The diagram of HHBa formation in 3 mM lipid/oil.

Figure 22:
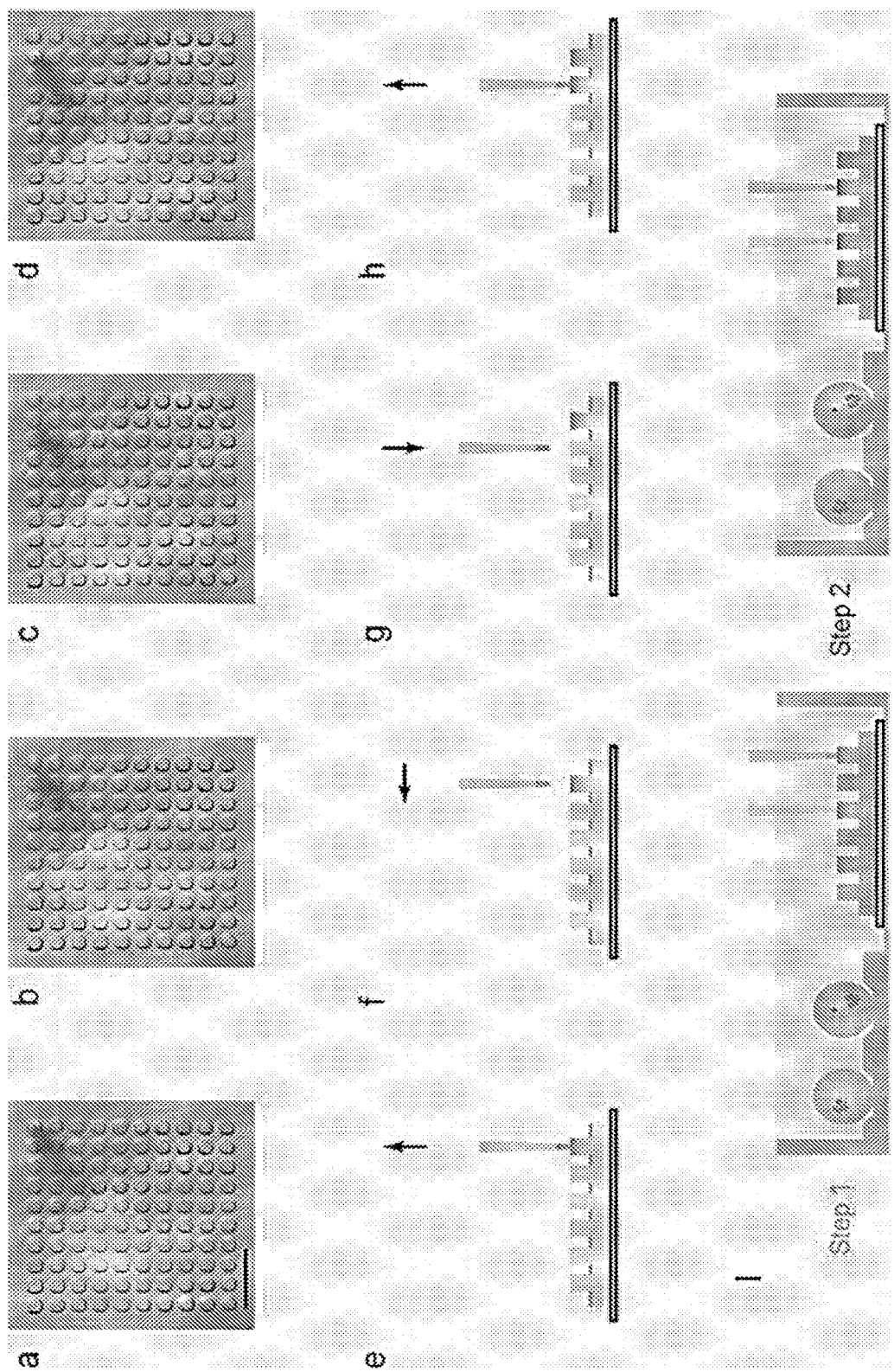

FIG. 22|Programmed chip loading with a home-made spotting robot. Biological samples can be selectively loaded/spotted onto the surface of the pillars with a sharp capillary tip on a spotting robot (Patchstar, Scientifica), which loads samples (αHL or DNA in source droplets) and spots them onto the pillars of the chip by physical contact. The loading/spotting is controlled by a labview program which enables automated and accurate positioning (up to 100 nm/step). a-d, Monitoring the sequential spotting. When the spotting tip is in physical contact with the pillar (a,d), the capillary apex is clearly visible as a focused spot. Scale bar: 210 µm. e-h, The cartoon diagram describing the spotting process consistent with the images above. The red colour at the end of the capillary represents the loaded biological samples. Biological samples are spotted onto the pillars by passive diffusion when the tip and the pillars are in physical contact. The spotting efficiency depends on various parameters (The initial sample concentration in the capillary; The spotting duration time; The diameter of the capillary tip) and is not particularly studied in this paper. The arrows indicate the movement direction of the capillary in the following step. I, Multi-sample spotting. In general, different types of biological samples can be loaded/spotted onto the same chip from various source droplets for biological screening in single molecule. Multi-sample spotting is done in multiple steps.

Figure 23:
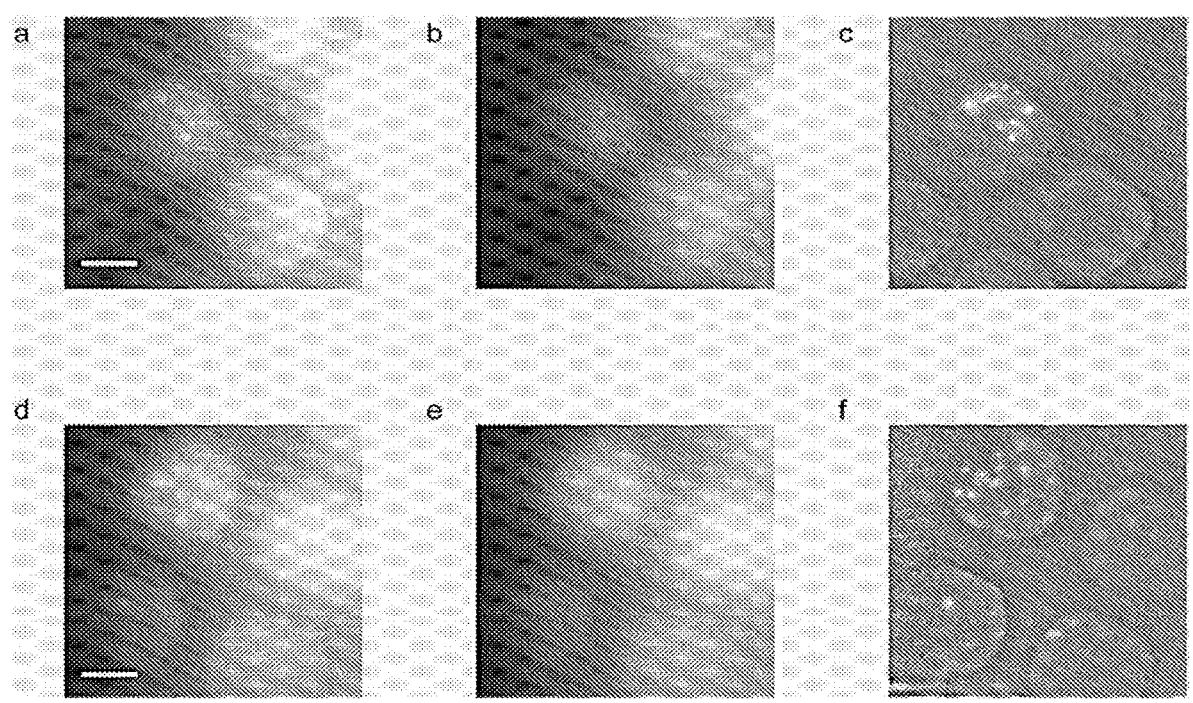

FIG. 23|Background normalization treatment. In the TIRF measurement of HHBa with full frame, background normalization treatment is normally needed to enhance the image contrast for optimized printing quality. Note that the background normalization is not performed for any quantitative data analysis and all the fluorescent traces being demonstrated in this study are extracted directly from the raw image data without any background treatment. a, A single frame from the raw image series. Scale bar: 35 µm. b, The background profile of a. The profile is generated by averaging 100 raw image frames followed with Gaussian filtration (ImageJ) to smooth the sharp features of the fluorescent spots. c, The image frame after background normalization (FIG. 3d). The normalization is done by dividing the raw image series with the background profile image (Image Calculator, ImageJ). To enhance the signal noise ratio, 12 subsequent frames are superimposed (Z project, ImageJ). d, A single frame from another image series. Scale bar: 35 µm. e, The corresponding background profile of d. f, The image frame after background normalization treatment.

Figure 24:
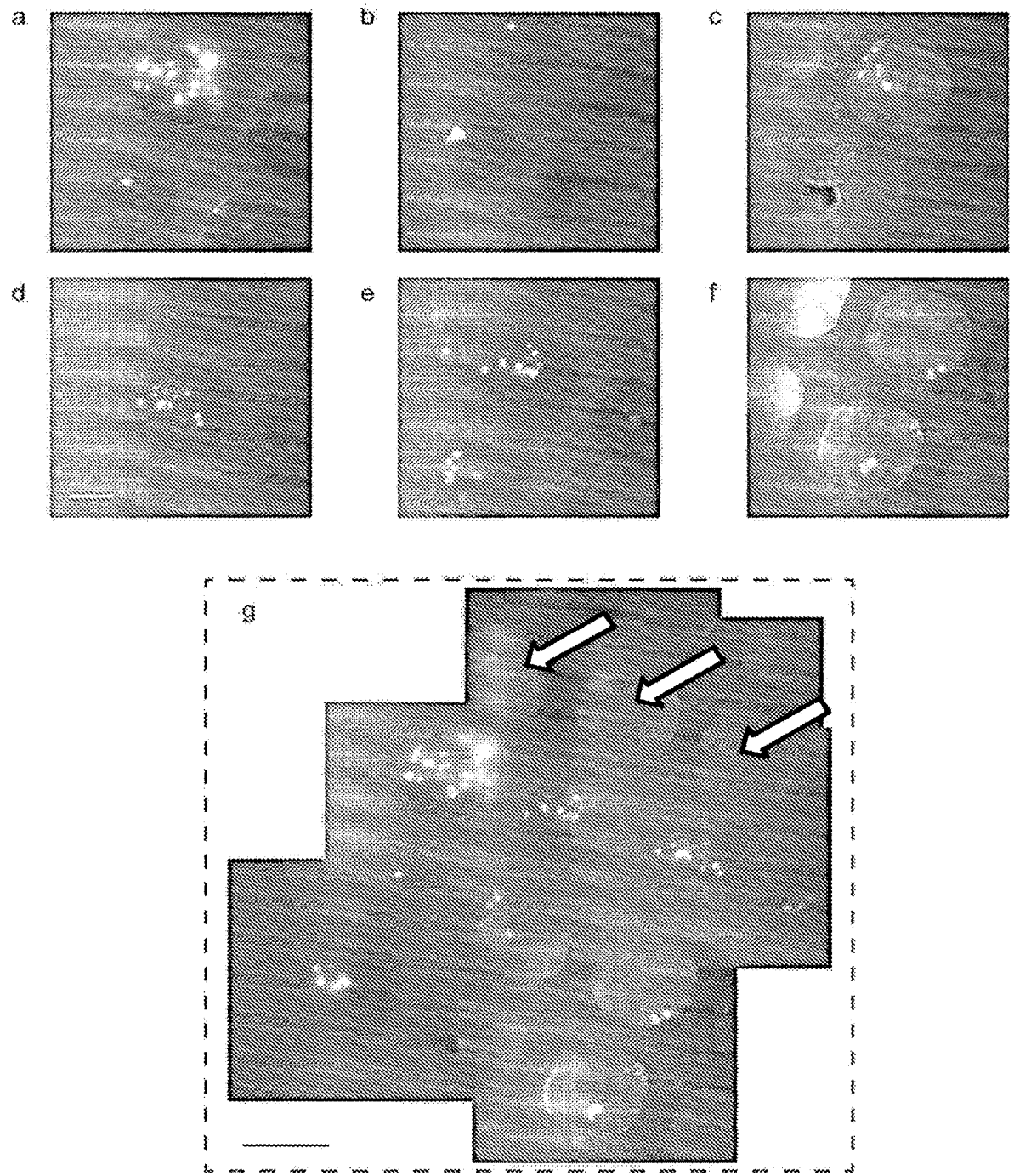

FIG. 24|Image stitching for expanded field of view. Due to the limited FOV (150 µm×150 µm) for a 60× oil immersion TIRF objective, only part of the HHBa chip (4/2500 bilayers) can be monitored simultaneously. To demonstrate an expanded area of the chip in TIRF mode, the objective is moved over different areas during the recording and a minimum 100 frames are recorded for each area. A standard deviation image (SDI) is calculated (Z-project, ImageJ) from each image series. Frequent intensity change of the fluorescent spots leads to large standard deviations in the pixel values and appear as white spots in the SDI. The SDI image treatment picks up specifically functioning nanopores and any scattering spots (fluorescent spots due to dusts or satellite droplets) with constant fluorescence will be emitted automatically. This treatment also minimizes the contrast difference between adjacent images to be stitched (MosaicJ, Fiji). a-f, A series of SDI in full frame for different parts of the array. Scale bar: 30 µm. g, The final stitched image from a-f. Unloaded HHBs are marked with arrows and no spots are visible. Scale bar: 50 µm.

EXAMPLE

Multiplexed Nucleic Acid Sensing Using an Optical Nanopore Array

To evaluate the feasibility and resolution of optical sequencing, in this study, prototypes of nucleic acid sensing with αHL nanopores are demonstrated using total internal reflection fluorescence (TIRF) microscopy. In general, αHL nanopores, which are placed on the Cis side of the bilayer, spontaneously insert into either a single droplet hydrogel bilayer (DHB) (FIG. 1b) or a hydrogel hydrogel bilayer array (HHBa) (FIG. 4b) and conduct $Ca^{2+}$ from the Trans side of the bilayer into the Cis. $Ca^{2+}$ binds with Fluo-8 in the Cis and emits fluorescence (517 nm) upon laser illuminations (473 nm). Clouds of Fluo-8/$Ca^{2+}$ appear as bright spots centred on each pore (FIG. 1d) and the fluorescence diminishes when away from the centre due to the competitive binding of $Ca^+$ with Ethylenediaminetetraacetic acid (EDTA) in the droplet or the HHBa chip. The average size of each spot at maximum intensity is around 3 µm in diameter and in principle over 2500 pores can be recorded simultaneously with an Electron Multiplying CCD camera (ixon3, Andor). The fluorescent intensity, which is proportional to the $Ca^{2+}$ flow rate, is enhanced at higher potentials (FIG. 8). Analytes (DNA or RNA) in the nanopore reduces $Ca^{2+}$ flow rate and the residual fluorescence (FIG. 1c, 2a) provides accurate information (1 pA equivalent amplitude resolution and 3 ms temporal resolution) for biological sensing.

To calibrate the amplitude resolution, a set of streptavidine tethered ssDNA with minor sequence differences ($C_{40}$, $X_3$ and $X_5$, Table 1) is designed as molecular rulers. Different lengths of abasic nucleotides are replaced in the sequence according to the position of the $2^{nd}$ recognition site of αHL [Stoddart, 2009 PNAS]. To perform optical recording, a DHB is formed (FIG. 1a) in 3 mM lipid/oil (Supplementary Materials) and nanopores in the droplet spontaneously insert into the bilayer.

At +100 mV, an open αHL in the DHB appears as a bright spot due to the abundant $Ca^{2+}$ being transported. Immediately, streptavidine tethered ssDNA blocks the pore and reduces the fluorescence (FIG. 1b) until the applied potential is flipped to negative. The normalized mean amplitude (Table 2) in phase II identifies the DNA being trapped in the pore. Repeated measurement cycles form a continuous fluorescent trace (FIG. 1e) and the events are accumulated for statistics. Compared with the results of patch clamp recording in a planar lipid membrane (PLM) (FIG. 14), the residual fluorescence and the residual current shows a linear relationship statistically (FIG. 1f) and the residual current separation between $X_3$ and $X_5$ demonstrates that OPC resolves ~1 pA equivalent resolution.

With up to ~300 Hz frame rate and ~1 pA amplitude resolution, optical detection should resolve fast kinetic process like miRNA unzipping in nanopores. miRNA, a short (~22 nucleotides) and non-coding RNA fragment, is of significant biological importance but difficult to be quantitatively analyzed by PCR based methods. The miRNA, when hybridized with a DNA probe and electrically stretched in a nanopore, can be forced to unzip. The unzipping kinetics, which is recorded from a single pore in the PLM, reveals the miRNA identity statistically [Wang, 2011 Nature Nano]. However, the unzipping duration time is widely distributed and requires a significant amount of events for statistics. Optical detection methods, which image pore activities in massive throughput and produce streams of single molecule fluorescent traces simultaneously, are ideal for ultra fast recording and screening of miRNA samples.

As a proof of concept demonstration, DNA probes with $C_{30}$ tags ("$C_{30}$" disclosed as SEQ ID NO: 1) (Plet7a and Plet7i) are designed to be sequence complimentary to their miRNA counterpart (Let7a and Let7i). All four combinations of hybridized miRNA with DNA probes are thermally annealed. A droplet (1.32 M KCL, 8.8 mM HEPES, 8.8 mM EDTA, Ph 7.0, 40 µM Fluo-8, 1.2 nM αHL) containing one type of Probe/miRNA (267 nM) forms a DHB with the substrate agarose in 3 mM lipid/oil as described in FIG. 1a.

At +160 mV constant bias, the fluorescent spots on each αHL "blinks" spontaneously when miRNA unzips and translocates through the pores. A typical unzipping event includes 3 blockage levels (FIG. 2a) and appears repetitively at a constant bias (FIG. 2c). Based on the optical recording results for all combinations of Probe/miRNA hybridizations and 2 types of miRNA controls, matched/unmatched Probe/miRNA generates long/short T1 duration time while T1 disappears in miRNA translocation events (FIG. 2b, d). Thus, it is concluded that T1 reflects the hybridization strength between the miRNA to the probe and is analyzed for miRNA identifications. T1 is widely distributed and can be fit by an exponential curve [Sauer-Budge, 2003 PhysRevLett]. The fitted rate constant (Table 5) is used to distinguish the miRNA identity.

Agarose, a low cost and bio-compatible hydrogel material, is widely used for gel electrophoresis and can be casted with micro-features [Mayer, 2004 Proteomics]. This hydrogel based chip device with micro-pillar structures (FIG. 3a) forms a HHBa (hydrogel-hydrogel bilayer array) with the substrate agarose in 3 mM lipid/oil (FIG. 3b, 4b).

Similar to a DHB, the HHBa can also be imaged by TIRF microscopy and each individual bilayer performs independent single molecule sensing (FIG. 3c). αHL can be selectively loaded into specific compartments of the HHBa. In a loaded bilayer, each inserted pore can be optically resolved as bright/dim fluorescent spots at +/−50 mV (FIG. 3d). Fluorescent traces from αHL and unloaded area show distinguishable signal patterns (FIG. 4e), which suggests the application of parallel recording of multiple samples in the same field of view for single molecule biological screening.

As demonstrated in the DHB system, streptavidine tethered ssDNA blocks αHL with unique blockage signals in the fluorescent traces. As a proof of concept experiment for biological screening, nanopore activities with/without DNA can be monitored simultaneously on the same HHBa chip in the same field of view. After spot loading and HHBa formation, αHL on the surface of the pillar inserts into the bilayer (FIG. 4b) and appear as bright fluorescent spots in loaded areas while the unloaded pillars maintain clean of spots (FIG. 4a). At +160 mV, streptavidine tethered $C_{40}$ blocks αHL and reduces fluorescent intensity of the spots. Single molecule fluorescent traces recorded simultaneously from HHBs with different loaded samples show clear discriminations (FIG. 4c) in the same field of view.

Besides the potential applications for biological screening, the HHBa chip also enlarges the total bilayer area (25 $mm^2$) with improved bilayer stability (>200 mV can be applied).

In conclusion, high resolution optical detection methods (~1 pA, ~3 ms) which monitor ion flux similar to electrical recording fits a wide range of nucleic acid sensing in nanopores as demonstrated herein. Being a highly parallel technology, the method is ideal for data intensive measurement, such as a nanopore array for human genome sequencing. With 3 µm pore to pore separation, an ideal hexagonal array of ~$10^6$ nanopores should function in parallel within a ~$mm^2$ area. A full human genome could be sequenced in 15 minutes with this throughput according to the reported nanopore sequence speed. Equipped with a more advanced hydrogel chip device, the applications of the method is expanded to more general single molecule biological screening. Technically, an OPC device doesn't require any high end electrical components as long as the voltage can be applied with macroscopic common electrodes. The demonstrated device (DHB and HHBa) is also made of extremely low cost and accessible materials. These technical advantages enable a chip device for single molecule biological sensing with extremely affordable price in a miniaturized size.

Summary

By optically encoding the $Ca^{2+}$ flux the detection of nucleic-acid binding events in nanopores was parrallelised. Parallel recordings at a density of ~$10^4$ $mm^{-2}$ measurements in a single droplet hydrogel bilayer (DHB) have been demonstrated. Both static DNA blockage and kinetic miRNA unzipping events can be monitored optically for single molecule nucleic acid identifications. Sub-pA equivalent amplitude resolution and 3 ms temporal resolution is demonstrated, which enables discrimination between nucleic acids with 2-4 bases difference. To further expand this platform, hydrogel hydrogel bilayer array (HHBa) is formed with micropatterned hydrogel chip, which is also compatible with a spotting robot for biological screening applications. Based on the enzymatic ratchet speed (~35 Hz), this optical recording platform should produce sequencing signal with a rate of $10^6$ nucleotides $mm^{-2}s^{-1}$, which paves the way to 15 minutes human genome sequencing and other general applications of single molecule sensing with nanopores.

Methods:

DHB formation. αHL (1.2 nM) and analytes (streptavidine tethered ssDNA or miRNA) (267 nM) are placed in a 350 nL droplet (1.32 M KCL, 8.8 mM HEPES, 8.8 mM EDTA, Ph 7.0, 40 µM Fluo-8), which is incubated in 3 mM 1,2-Diphytanoyl-sn-glycero-3-phosphocholine (DPhPC) in oil (Supplementary Materials) to form an external lipid monolayer coating. The droplet is pipette transferred into the measurement chamber (FIG. 1a, FIG. 5), where a thin layer (~200 nm) of agarose (0.66 M $CaCl_2$, 8.8 mM HEPES, Ph 7.0) is spin coated (3000× rpm, 30 s) on the coverslip and is incubated in 3 mM DPhPC in oil. The lipid coated droplet, upon contact with the agarose, spontaneously forms a single DHB. The ground electrode (Ag/AgCl), which forms a closed circuit with the electrode (Ag/AgCl) in the agarose, is stabbed into the droplet. The voltage protocols are applied with a patch clamp amplifier (Axopatch 200B, Molecular Devices). αHL inside the droplet spontaneously inserts into DHB and the ion transport is detected both electrically (FIG. 6) and optically (FIG. 1d).

HHBa Measurements. Upon finishing loading, the chip is flipped and placed on the electrode (FIG. 3b, FIG. 21) and the HHBa forms spontaneously when the chip is annealed with the substrate agarose in 3 mM lipid/oil. The voltage protocols are applied with a patch clamp amplifier (Axopatch 200B, Molecular Devices). Nanopore activities in the HHBa can be monitored with TIRF microscopy. 30 ms exposure time is normally used to compensate the lower signal/noise ratio in a HHBa measurement. Due to the limited field of view, only 4 compartments in a HHBa chip can be recorded simultaneously.

Supplementary Materials

The lipid/oil used in this paper is defined as 1,2-Diphytanoyl-sn-glycero-3-phosphocholine (DPhPC) (Avanti Polar Lipids) dissolved in oil.

Oil: 1:1 (v:v) mixture of hexadecane (Sigma-Aldrich) and silicone oil AR20 (Sigma-Aldrich).

To dissolve lipid in oil, the DPhPC powder is first dissolved in pentane (Sigma-Aldrich) in a 7 mL glass vial. It is then air dried with nitrogen gas to form a thin film of lipid on the inner wall of the vial. The lipid film is desiccator treated for more than 4 hours to remove the residual pentane. Finally the lipid film is dissolved in the oil.

Ethylenediaminetetraacetic acid (EDTA) (Sigma-Aldrich), agarose for routine use (Sigma-Aldrich), agarose low melting point (Sigma-Aldrich), 4-(2-hydroxyethyl)-1-piperazineethanesulfonic acid (HEPES) (Sigma-Aldrich), Potassium Chloride (Sigma-Aldrich), Calcium Chloride (Sigma-Aldrich), Pentane (Sigma-Aldrich), SU-8 2035 photoresist (MicroChem), Poly-methylmethacrylate (PMMA 495 a5) (MicroChem), Poly-dimethylsiloxane (PDMS, Sylgard 184) (Dow Corning), Fluo-8 (ABD Bioquest), Chelex (BioRadchelex 100 Resin, Biotechnology Grade, 100-200 mesh), Streptavidine (New England Biolabs) were used as received without further purification.

DNA (ATDbio) and RNA (IDTDNA) samples were purchased with HPLC purification service and used without further purification.

The protein nanopores used in this paper are αHL WT. The αHL heptamer protein is E. coli expressed and purified based on the published protocols[1].

Supplementary Methods

1|Buffer Preparation

Both the potassium chloride buffer (1.5 M KCl, 10 mM HEPES, PH 7.0) and the calcium chloride buffer (0.75 M CaCl2, 10 mM HEPES, PH 7.0) were prepared and membrane filtered (0.2 µm cellulose acetate, Nalgene) prior to use. The potassium chloride buffer used in any fluorescence measurement needs to be treated with Chelex 100 resin for overnight to minimize the divalent cation contaminations.

2|DNA Sample Preparation

DNA samples are dissolved in DNase/RNase free water prior to use. Streptavidine and biotinylated ssDNA (C40, X3 or X5) are mixed with 1:1 molar ratio in the potassium chloride buffer (1.5 M KCl, 10 mM EDTA, 10 mM HEPES, PH 7.0, chelex treated) and incubated at 4° C. for 20 min to form the biotin/streptavidine tethering.

3|miRNA/Probe Annealing miRNA samples are dissolved in DNase/RNase free water prior to use. The miRNA and the probe are mixed with 1:1 molar ratio in the potassium chloride buffer (1.5 M KCl, 10 mM EDTA, 10 mM HEPES, PH 7.0, chelex treated). To form probe/miRNA hybridization, the mixed solution is heated to 95° C. for 5 min and gradually cooled down from 65° C. to 25° C. with a rate of −5° C./min in a thermal cycler (Veriti, Life Technologies).

4|TIRF Microscopy

TIRF measurements are performed with a Nikon Eclipse Ti microscope equipped with a 60× oil immersion objective (Plan Apo TIRF, Nikon). The fluorescence is excited by a 473 nm Argon ion laser (Shanghai Dream Laser Technologies) and imaged with an electron-multiplying CCD camera (Ixon3, Andor). In the TIRF recording, the full field of view is 150 µm by 150 µm. Parameters like the exposure time, EM gain and the binning size are optimized to achieve the best S/N ratio in specific recordings. The highest recording rate that has been tested is 3 ms/frame.

5|Fluorescent Trace Extraction and Normalization

The fluorescent images are recorded in .sif format (Andor Solis) and analyzed by a home-made labview program. The program performs data analysis numerically by analyzing the raw image files as pixel values in a data array. The fluorescent trace can be extracted by either adding up the pixel values of the fluorescent spots or by 2d Gaussian fitting. Due to the long computation time of the fitting, all the fluorescent traces in this paper are extracted by adding up the pixel values. 2d Gaussian fitting is performed only for demonstration (FIG. 9) and tracking (FIG. 10). To minimize fluctuations from the laser illumination, the fluorescent intensity is normalized by the background fluorescence around the pore (a donut shaped local background area) and this will get rid of most low frequency fluctuations in the fluorescent trace. The absolute value of OPC readout has huge measurement variations due to the different optics conditions from time to time. However, by normalizing the fluorescent trace with reference levels, such as the open pore fluorescence at −50 mV and 0 mV (Fref0 and Fref1), this variation is significantly minimized. This normalization process follows the formula below.

$$F_{norm} = \frac{F_{raw} - F_{ref0}}{F_{ref1} - F_{ref0}}$$

6|Planar Bilayer Measurements

Planar Lipid Membrane measurement is performed similar to the method published before2. Briefly, lipid (DPhPC) bilayer forms across a Teflon (Good Fellow, 25 µm thick) aperture, which separates the Cis (electrically grounded) and the Trans chamber of the measurement apparatus (1 mL volume on both sides). Ionic current through a single αHL in the PLM is patch-clamp recorded (Axopatch 200B, Molecular Devices) with a sampling rate of 5 kHz (Digidata 1440A digitizer, Molecular Devices) and is low-pass filtered at 1 kHz. Streptavidine tethered ssDNA (267 nM) is added to the Cis chamber and the chamber is magnetically stirred to achieve homogeneous sample distribution. Voltage protocols (100 mV, 0.9 sec; −140 mV, 0.05 sec; 0 mV, 0.05 sec) are repeated 1000 times to accumulate enough events for statistics. To mimic the optical recording measurement, the PLM is recorded with asymmetric buffer condition (Cis: 1.32 M KCl, 8.8 mM HEPES, Ph 7.0; Trans: 0.66 M CaCl2, 8.8 mM HEPES, Ph: 7.0).

7|Photolithography

The photomask is designed (AutoCAD) and printed on a transparent film (JDphoto). Micropatterns of SU-8 pillars are fabricated according to the standard photolithography protocols (MicroChem):

1. Spin coating: 1 mL of SU-8 2035 photoresist is spin coated on the 6-inch silicon wafer with the speed of 500 rpm for 15 seconds followed with 2000 rpm for 35 seconds.

2. Pre-bake: The wafer is baked at 60° C. for 2.5 minutes and 95° C. for 7 minutes 3. Exposure: The wafer, which is covered with the photomask, is UV exposed (200 mJ/cm2) for 30 seconds.

4. Develop: The wafer is then sprayed and washed with the developer for 6 minutes.

5. Wash: The developed wafer is cleaned with isopropanol and air dried with nitrogen streams.

6. Hard Bake: The wafer is baked at 150° C. for 10 min to finalize the lithography process.

The thickness of the fabricated pillar structures is around 40 μm according to the protocol (MicroChem) and the micropatterned wafer can be re-used for multiple times in the following soft lithography process.

8|Soft Lithography

The soft lithography process is performed according to the published protocols[3]. Briefly, PDMS base and the curing agent are mixed with 10:1 volume ratio. The mixture is poured over the micropatterned silicon wafer mould in a petri-dish and degassed for 1 hour. The PDMS mixture with the mould is then incubated in the 80° C. oven for 4 hours to get fully casted. The casted PDMS elastomer can be peeled off from the wafer. This PDMS mould can be re-used for multiple times in the following hydrogel chip fabrication process (FIG. 20).

Supplementary Discussions

1|Pore Densities Estimation (Theoretical Limit)

Assuming that the pores are assembled into an ideal hexagonal array, each hexagonal unit cell contains 1+3×(1/6)=3 nanopores. If the pore to pore distance is d, then the area of each unit cell is:

$$\text{Area} = \frac{3\sqrt{3}}{2} d^2 \qquad (1)$$

The area per pore is:

$$\text{Area/pore} = \frac{\sqrt{3}}{2} d^2 \qquad (2)$$

According to the half height width of each pore (FIG. 11), the minimum pore to pore separation for independent optical recording is d=3 μm.

The estimated pore density is:

$$N = \frac{(10^{-3})^2}{\frac{\sqrt{3}}{2}(3 \times 10^{-6})^2} = 1.3 \times 10^5 \text{ pores} \cdot \text{mm}^{-2} \qquad (3)$$

2|Pore Densities Estimation

The bilayer analysis in this study is performed with a larger pore to pore separation ~10 μm (FIG. 1d). The recording density is estimated as:

$$N = 1.16 \times 10^4 \text{ pores} \cdot \text{mm}^{-2} \qquad (4)$$

3|Sequencing Densities

Based on published results[4, 5] the nanopore sequencing speed could achieve up to 40 nucleotides per second. With a hexagonal nanopore array of 3 μm pore to pore separation, one can simply estimate the sequencing data production rate as below

$$40 \times 1.3 \times 10^5 = 5.2 \times 10^6 \text{ nucleotides} \cdot \text{mm}^{-2} \qquad (5)$$

In principle, for the size of a human genome (~3×10⁹ nucleotides), the sequencing can be finished in ~15 min (900 s) within a ~mm² sized array.

4|Unzipping Kinetics Modelling

The miRNA unzipping kinetics is modelled similar as reported before[6, 7]. To minimize the parameters, the modelling of the unzipping process is simplified as a single step, first-order reaction as below and fits to the experiment results well (FIG. 2e). The rate constant from state A (hybridized state) to state B (unzipped state) is defined to be k.

$$A \xrightarrow{k} B \qquad (6)$$

In a macroscopic reaction, $$\frac{d[A]}{dt} = -k[A] \qquad (7)$$

$$\frac{d[B]}{dt} = k[A] \qquad (8)$$

The solutions to the above equations are:

$$[A] = [A_0]e^{-kt} \qquad (9)$$

$$[B] = [A_0](1 - e^{-kt}) \qquad (10)$$

$$\frac{d[B]}{dt} = [A_0]ke^{-kt} \qquad (11)$$

In single molecule kinetics, the probability density function (p.d.f.) for a single molecule which has changed from state A to B between the time interval is t→t+Δt:

$$p.d.f(t) = \frac{d[B]}{[A_0]dt} = ke^{-kt} \qquad (12)$$

The rate constant k, which reflects the hybridization strength between the miRNA and the probe, is a function of the temperature (T) and the applied potential (V):

$$k(T, V) = k_0 \exp\left(-\frac{E_a - q_{\textit{eff}} V}{k_B T}\right) \quad (13)$$

Here $k_B$, is the Boltzmann constant ($8.62 \times 10^{-5}$ eV/K).

We assume that the unzipping process is driven by a constant electrical force. And the effective charge ($q_{\textit{eff}}$) maintains constant during the whole unzipping process. Under the applied potential, the effective activation energy ($E_a$) is lowered by $q_{\textit{eff}} V$.

By rearranging equation (13):

$$\ln(k) = \frac{q_{\textit{eff}}}{k_B T} V - \frac{E_a}{k_B T} + \ln(k_0) \quad (14)$$

It is obvious that and V have a linear relationship and the fitted slope equals to $$\frac{q_{\textit{eff}}}{k_B T}.$$

From the voltage dependence results, the fitted slope (a) equals to 22.0 ln (s$^{-1}$) Assuming that T=300K:

$$q_{\textit{eff}} = \alpha k_B T = 0.57e \quad (15)$$

The qualitative model suggested here is too simple for accurate estimation of the effective charge. It is also believed that the effective charge is estimated lower due to the different environment inside a nanopore than in the buffer[6].

TABLE 1

The nucleic acid abbreviations and sequences. "X" in the sequence represents the abasic DNA nucleotide. Table discloses SEQ ID NOS 2-8, respectively, in order of appearance.

| Abbreviations | Nucleic Acid Sequence |
|---|---|
| $X_5$ | 3'-Biotin-TEG-CCCCCCCCCCCCCCCCCCCCCCCCCCCCCCXXXXXCCCCCCCCCC-5' |
| $X_3$ | 3'-Biotin-TEG-CCCCCCCCCCCCCCCCCCCCCCCCCCCCCCXXXCCCCCCCCCCCC-5' |
| $C_{40}$ | 3'-Biotin-TEG-CCCCCCCCCCCCCCCCCCCCCCCCCCCCCCCCCCCCCCCC-5' |
| Plet7a | 3'-C-ACTCCATCATCCAACATATCAA-C-5' |
| Plet7i | 3'-C-ACTCCATCATCAAACACCATCAA-C-5' |
| Let7a | 3'-UUGAUAUGUUGGAUGGAUGGAGU-5' |
| Let7i | 3'-UUGUCGUGUUUGAUGAUGGAGU-5' |

TABLE 2

The statistics of the residual fluorescence by DNA blockages. The fluorescent amplitude is normalized according to the two reference levels (open pore fluorescence at 0 mV and −50 mV).

|  | Mean Fluorescent Intensity/a.u. | Standard Deviation/a.u. | Counts |
|---|---|---|---|
| $C_{40}$ | 0.38684 | 0.08433 | 132 |
| $X_3$ | 0.56737 | 0.06964 | 140 |
| $X_5$ | 0.68791 | 0.07229 | 121 |

TABLE 3

The statistics of the residual current by DNA blockages. The mean residual current and standard deviation is calculated from the Gaussian fitting of the histogram (FIG. 14).

|  | Mean Residual Correct/pA | Standard Deviation/pA |
|---|---|---|
| $C_{40}$ | 8.02 | 0.13 |
| $X_3$ | 9.49 | 0.11 |
| $X_5$ | 10.46 | 0.12 |

TABLE 4

The statistics of the mean duration time for a full miRNA unzipping cycle. The large standard deviation is resulted from the exponential distribution of the duration times.

|  | T1/ms | σT1/ms | T2/ms | σT2/ms | T3/ms | σT3/ms | Counts |
|---|---|---|---|---|---|---|---|
| Plet7i/Let7i | 393.41 | 769.20 | 957.40 | 1287.51 | 125.63 | 284.87 | 541 |
| Plet7i/Let7a | 39.13 | 134.21 | 306.14 | 506.16 | 49.25 | 73.55 | 350 |
| Plet7a/Let7i | 315.98 | 695.61 | 521.73 | 781.33 | 84.2 | 230.37 | 378 |
| Plet7a/Let7i | 43.6 | 109.59 | 476.17 | 660.77 | 90.86 | 273.04 | 561 |
| Let7i | 0 | 0 | 632.15 | 1263.18 | 123.37 | 177.75 | 87 |
| Let7a | 0 | 0 | 707.22 | 786.37 | 47.67 | 113.23 | 59 |

TABLE 5

The rate constants for different Probe/miRNA combinations. The rate constant is calculated from the exponential fitting of the histogram for T1 (FIG. 2e). Sequence complimentary hybridizations between probe and miRNA generate low rate constant values while the unmatched counterparts generate high rate constant values.

|  | Plet7a/Let 7a | Plet7i/Let 7a | Plet7i/Let 7i | Plet7a/Let 7i |
|---|---|---|---|---|
| Rate Constant/s$^{-1}$ | 13.66 | 68.80 | 7.06 | 47.45 |

SUPPLEMENTARY REFERENCES

1. Castell, O. K., Berridge, J. & Wallace, M. I. Quantification of Membrane Protein Inhibition by Optical Ion Flux in a Droplet Interface Bilayer Array. Angewandte Chemie-International Edition 51, 3134-3138 (2012).
2. Stoddart, D., Heron, A. J., Mikhailova, E., Maglia, G. & Bayley, H. Single-nucleotide discrimination in immobilized DNA oligonucleotides with a biological nanopore. Proceedings of the National Academy of Sciences of the United States of America 106, 7702-7707 (2009).
3. Qin, D., Xia, Y. N. & Whitesides, G. M. Soft lithography for micro- and nanoscale patterning. Nature Protocols 5, 491-502 (2010).
4. Manrao, E. A. et al. Reading DNA at single-nucleotide resolution with a mutant MspA nanopore and phi29 DNA polymerase. Nature Biotechnology 30, 349-U174 (2012)
5. Cherf, G. M. et al. Automated forward and reverse ratcheting of DNA in a nanopore at 5-angstrom precision. Nature Biotechnology 30, 344-348 (2012).
6. Sauer-Budge, A. F., Nyamwanda, J. A., Lubensky, D. K. & Branton, D. Unzipping kinetics of double-stranded DNA in a nanopore. Physical Review Letters 90, 238101 (2003).
7. Jin, Q., Fleming, A. M., Burrows, C. J. & White, H. S. Unzipping Kinetics of Duplex DNA Containing Oxidized Lesions in an alpha-Hemolysin Nanopore. Journal of the American Chemical Society 134, 11006-11011 (2012).
8. Leptihn, S. et al. Constructing droplet interface bilayers from the contact of aqueous droplets in oil. Nature Protocols 8, 1048-1057 (2013).
9. Mayer, M., Yang, J., Gitlin, I., Gracias, D. H. & Whitesides, G. M. Micropatterned agarose gels for stamping arrays of proteins and gradients of proteins. Proteomics 4, 2366-2376 (2004).

The invention claimed is:

1. A bilayer array comprising:
opposing hydrogel surfaces provided by a first component comprising an array of discrete hydrogel surfaces opposing a hydrogel surface of a second component, wherein the second component comprises a hydrogel layer;
wherein the opposing hydrogel surfaces are immersed in a hydrophobic medium comprising amphipathic molecules, and wherein the opposing hydrogel surfaces are spaced apart sufficiently to provide bilayers of the amphipathic molecules formed therebetween;
channel molecules in the bilayers;
a means arranged to provide a membrane potential across the bilayers.

2. The bilayer array of claim 1, wherein the array of hydrogel surfaces is provided on an array of pillars extending from the first component.

3. The bilayer array of claim 2, wherein the pillars comprise and/or are formed of a hydrogel.

4. The bilayer array according to claim 2, wherein the first component comprising an array of hydrogel surfaces further comprises a barrier material arranged to prevent cross-contamination of reagents and/or channel molecules between adjacent hydrogel surfaces, wherein the barrier material is arranged between the pillars.

5. The bilayer array according of claim 1, wherein a discrete hydrogel surface of the first component is less than about 200 microns in diameter.

6. The bilayer array of claim 5, wherein a discrete hydrogel surface of the first component is about 100 microns in diameter, or less.

7. The bilayer array of claim 1, wherein the total bilayer area provided by the array of bilayers is at least 1 mm$^2$.

8. The bilayer array of claim 1, wherein the first component comprising an array of hydrogel surfaces further comprises a barrier material arranged to prevent cross-contamination of reagents and/or channel molecules between adjacent hydrogel surfaces.

9. The bilayer array of claim 8, wherein the barrier material is arranged between the hydrogel surfaces.

10. The bilayer array of claim 1, wherein the first component is supported by a plate.

11. The bilayer array of claim 1, wherein the second component comprises a plate.

12. The bilayer array of claim 1, wherein the means for providing a membrane potential comprises cathode and anode electrodes.

13. The bilayer array of claim 1, wherein the bilayer array comprises only a single set of anodes and cathodes for providing membrane potential across all the bilayers in the array.

14. The bilayer array of claim 1, wherein the hydrogel comprises or consists of less than 5% (w/v) agarose.

15. The bilayer array of claim 1, wherein the first component hydrogel comprises a potassium chloride buffer and the second component hydrogel comprises a calcium chloride buffer; or vice versa.

16. The bilayer array of claim 15, wherein the buffer further comprises EDTA.

17. The bilayer array according to claim 1, wherein each channel molecule of the channel molecules comprises a nanopore.

18. The bilayer array according to claim 1, wherein each channel molecule of the channel molecules comprises a biological molecule.

19. The bilayer array according to claim 18, wherein the biological molecule is a pore-forming protein.

20. The bilayer array according to claim 1, wherein each channel molecule of the channel molecules comprises alpha-hemolysin.

21. A method for optical polymer sequencing with a nanopore held in a bilayer of amphipathic molecules, wherein the bilayer is provided in a bilayer array according to claim 20, the method comprising:
  providing a bilayer of amphipathic molecules, wherein the bilayer comprises one or more nanopores;
  providing a first signal-associated molecule on one side of the bilayer, wherein the first signal-associated molecule is capable of flux through the nanopore(s) by the action of a membrane potential across the bilayer;
  providing a second signal-associated molecule on the opposing side of the bilayer relative to the first signal-associated molecule, wherein the first and second signal associated molecules are arranged to emit an optical signal when in contact;
  providing a polymer on at least one side of the bilayer;
  applying a membrane potential across the bilayer such that the first signal-associated molecule is transported through the nanopore and interacts with the second signal-associated molecule to emit an optical signal;
  detecting the optical signal; and
  detecting any modification, or lack thereof, in the optical signal as the flux of the first signal-associated molecule is modified by at least partial blocking of the nanopore by the polymer as it interacts with the nanopore,
  whereby the polymer is sequenced.

22. A method of manufacturing a bilayer array comprising
  providing a mould for casting a hydrogel first component, wherein the mould comprises an array of cavities for forming the hydrogel first component with an array of hydrogel pillars;
  pouring a liquid arranged to set into a hydrogel into the mould;
  laying a plate onto the surface of the liquid and setting the liquid to form the hydrogel first component;
  removing the mould from the hydrogel first component;
  optionally coating a barrier material on the hydrogel first component, between the hydrogel pillars;
  adding a reagents and/or samples to one or more hydrogel pillars;
  providing a second component comprising a hydrogel surface on a plate;
  submerging the hydrogel surfaces of the first and second components in a volume of hydrophobic medium comprising amphipathic molecules, thereby forming a monolayer of amphipathic molecules on the hydrogel surfaces of the first and second components;
  bringing the first and second components into an opposing position relative to each other such that the monolayers of amphipathic molecules form a bilayer.

* * * * *

SEQUENCE LISTING

<160> NUMBER OF SEQ ID NOS: 11

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
cccccccccc cccccccccc cccccccccc                                      30

<210> SEQ ID NO 2
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (12)..(16)
<223> OTHER INFORMATION: Abasic nucleotide

<400> SEQUENCE: 2 ccccccccccc cnnnnnccccc cccccccccc cccccccccc cccccccccc              50

```
<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(15)
<223> OTHER INFORMATION: Abasic nucleotide

<400> SEQUENCE: 3
cccccccccc ccnnncccccc cccccccccc cccccccccc cccccccccc                50

<210> SEQ ID NO 4
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cccccccccc cccccccccc cccccccccc cccccccccc cccccccccc                50

<210> SEQ ID NO 5
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cccccccccc cccccccccc cccccccccc aactatacaa cctactacct caccccccccc     60 cccccccccc cccccccccc cc                                              82

<210> SEQ ID NO 6
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cccccccccc cccccccccc cccccccccc aacagcacaa actactacct cacccccccc      60
cccccccccc cccccccccc cc                                              82

<210> SEQ ID NO 7
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
ugagguagua gguuguauag uu                                              22

<210> SEQ ID NO 8
<211> LENGTH: 22
<212> TYPE: RNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 8
ugagguagua guuugugcug uu                                              22

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(29)
<223> OTHER INFORMATION: Abasic nucleotide

<400> SEQUENCE: 9
cccccccccc cccccccccc ccccnnnnnc cccccccccc                           40

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(28)
<223> OTHER INFORMATION: Abasic nucleotide

<400> SEQUENCE: 10
cccccccccc cccccccccc cccccnnncc cccccccccc                           40

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cccccccccc cccccccccc cccccccccc cccccccccc                           40
```